(12) United States Patent
Kubota et al.

(10) Patent No.: US 11,766,685 B2
(45) Date of Patent: Sep. 26, 2023

(54) ULTRAFINE BUBBLE GENERATING METHOD, ULTRAFINE BUBBLE-CONTAINING LIQUID MANUFACTURING APPARATUS AND MANUFACTURING METHOD, AND ULTRAFINE BUBBLE-CONTAINING LIQUID

(71) Applicant: CANON KABUSHIKI KAISHA, Tokyo (JP)

(72) Inventors: Masahiko Kubota, Tokyo (JP); Kenji Takahashi, Yokohama (JP); Ikuo Nakazawa, Kawasaki (JP); Akitoshi Yamada, Yokohama (JP); Nobuhisa Tanahashi, Tokyo (JP); Yoshio Kinoshita, Tokyo (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 700 days.

(21) Appl. No.: 16/642,432

(22) PCT Filed: Aug. 29, 2018

(86) PCT No.: PCT/JP2018/031975
§ 371 (c)(1),
(2) Date: Feb. 27, 2020

(87) PCT Pub. No.: WO2019/044913
PCT Pub. Date: Mar. 7, 2019

(65) Prior Publication Data
US 2020/0254468 A1 Aug. 13, 2020

(30) Foreign Application Priority Data

Aug. 31, 2017 (JP) .................................. 2017-167594
Aug. 7, 2018 (JP) .................................. 2018-148537

(51) Int. Cl.
*B05B 7/16* (2006.01)
*A01N 25/02* (2006.01)
(Continued)

(52) U.S. Cl.
CPC ............ *B05B 7/1686* (2013.01); *A01N 25/02* (2013.01); *A61L 2/183* (2013.01); *C02F 1/02* (2013.01);
(Continued)

(58) Field of Classification Search
None
See application file for complete search history.

(56) References Cited

U.S. PATENT DOCUMENTS

| 5,808,647 A | 9/1998 | Kurata et al. |
| 6,443,561 B1 | 9/2002 | Murakami |

(Continued)

FOREIGN PATENT DOCUMENTS

| CN | 1840231 A | 10/2006 |
| CN | 101721929 A | 6/2010 |

(Continued)

OTHER PUBLICATIONS

S. Calgaroto et al., "On the Nanobubbles Interfacial Properties and Future Applications in Flotation," 60 Miner. Eng. 33-40 (Feb. 2014) (XP028841925).

(Continued)

*Primary Examiner* — Richard C Gurtowski
(74) *Attorney, Agent, or Firm* — VENABLE LLP

(57) ABSTRACT

Ultrafine bubbles with a diameter of less than 1.0 μm are generated in liquid by causing film boiling in liquid by means of a heater.

8 Claims, 23 Drawing Sheets

(51) Int. Cl.
*A61L 2/18* (2006.01)
*C02F 1/02* (2023.01)
*C02F 1/78* (2023.01)
*C11D 3/48* (2006.01)
*B05B 15/40* (2018.01)

(52) U.S. Cl.
CPC .............. *C02F 1/78* (2013.01); *C11D 3/48* (2013.01); *B05B 15/40* (2018.02); *C02F 2303/04* (2013.01)

(56) References Cited

U.S. PATENT DOCUMENTS

| | | | |
|---|---|---|---|
| 6,471,350 | B2 | 10/2002 | Katsuragi et al. |
| 8,356,885 | B2 | 1/2013 | Silverbrook et al. |
| 8,740,450 | B2 | 6/2014 | Mogami et al. |
| 9,085,143 | B2 | 7/2015 | Ishida et al. |
| 10,293,309 | B2 | 5/2019 | Tachibana et al. |
| 10,632,506 | B2 | 4/2020 | Tachibana |
| 2001/0043247 | A1* | 11/2001 | Tajima .............. B41J 2/16 347/20 |
| 2006/0051214 | A1 | 3/2006 | Ussing |
| 2007/0189972 | A1* | 8/2007 | Chiba .............. B01F 23/238 424/9.52 |
| 2008/0117255 | A1 | 5/2008 | Cannon et al. |
| 2010/0103216 | A1 | 4/2010 | Silverbrook et al. |
| 2011/0063372 | A1 | 3/2011 | Grant et al. |
| 2014/0273155 | A1 | 9/2014 | Miyao et al. |
| 2014/0327720 | A1* | 11/2014 | Choy .............. B41J 2/1433 239/302 |
| 2015/0167959 | A1 | 6/2015 | Cho et al. |
| 2015/0343399 | A1 | 12/2015 | Kim et al. |
| 2016/0319209 | A1 | 11/2016 | Shiode et al. |
| 2020/0238654 | A9 | 7/2020 | Tachibana |

FOREIGN PATENT DOCUMENTS

| | | | |
|---|---|---|---|
| CN | 104296578 | A | 1/2015 |
| CN | 105228736 | A | 1/2016 |
| CN | 105258264 | A | 1/2016 |
| CN | 105363504 | A | 3/2016 |
| CN | 106463387 | A | 2/2017 |
| EP | 0 684 134 | A2 | 11/1995 |
| EP | 1 078 757 | A2 | 2/2001 |
| GB | 2298395 | A | 9/1996 |
| JP | 5-185680 | A | 7/1993 |
| JP | 2000-189946 | A | 7/2000 |
| JP | 2001-130005 | A | 5/2001 |
| JP | 2002-137399 | A | 5/2002 |
| JP | 2005-538287 | A | 12/2005 |
| JP | 2007-136255 | A | 6/2007 |
| JP | 2008-030002 | A | 2/2008 |
| JP | 2008-183502 | A | 8/2008 |
| JP | 2009-297654 | A | 12/2009 |
| JP | 4456176 | B2 | 4/2010 |
| JP | 2011-020005 | A | 2/2011 |
| JP | 2014-171463 | A | 9/2014 |
| JP | 2016-165431 | A | 9/2016 |
| JP | 6118544 | B2 | 4/2017 |
| RU | 2553105 | C1 | 6/2015 |
| RU | 2578122 | C2 | 3/2016 |
| SU | 1171116 | A1 | 8/1985 |
| WO | 2013/062054 | A1 | 5/2013 |
| WO | 2015/048904 | A1 | 4/2015 |
| WO | 2016/088731 | A1 | 6/2016 |
| WO | 2018/148247 | A1 | 8/2018 |
| WO | 2019/044631 | A1 | 3/2019 |

OTHER PUBLICATIONS

Official Action in Russian Application No. 2020108194 (dated Apr. 2021).
Examination report No. 2 in Australian Application No. 2018323492 (dated Jul. 2021).
First Office Action in Chinese Application No. 201880055620.1 (dated Dec. 2020).
Office Action in Russian Application No. 2020108194 (dated Sep. 2020).
Examination Report in Indian Application No. 202047008069 (dated Jul. 2020).
Written Opinion and Search Report in Singapore Application No. 11202001745U (dated Sep. 2020).
Examination Report No. 1 in Australian Application No. 2018323492 (dated Jan. 2021).
Second Office Action in Chinese Application No. 201880055620.1 (dated Sep. 2021).
Notification of Reason for Refusal in Korean Application No. 10-2020-7005744 (dated Jun. 2021).
Notice of Reasons for Refusal in Japanese Application No. 2018-148537 (dated Aug. 2022).
Takahashi et al., U.S. Appl. No. 16/642,426, filed Feb. 27, 2020.
Kubota et al., U.S. Appl. No. 16/802,685, filed Feb. 27, 2020.
Ozaki et al., U.S. Appl. No. 16/802,672, filed Feb. 27, 2020.
Arimizu et al., U.S. Appl. No. 16/802,675, filed Feb. 27, 2020.
Imanaka et al., U.S. Appl. No. 16/802,688, filed Feb. 27, 2020.
Imanaka et al., U.S. Appl. No. 16/802,693, filed Feb. 27, 2020.
Ishinaga et al., U.S. Appl. No. 16/802,680, filed Feb. 27, 2020.
Yanai et al., U.S. Appl. No. 16/802,677, filed Feb. 27, 2020.
Ozaki et al., U.S. Appl. No. 16/802,667, filed Feb. 27, 2020.
Imanaka et al., U.S. Appl. No. 16/802,661, filed Feb. 27, 2020.
Imanaka et al., U.S. Appl. No. 16/802,652, filed Feb. 27, 2020.
Examination Report No. 1 in Australian Application No. 2022200611 (dated Feb. 2023).
International Preliminary Report on Patentability in International Application No. PCT/JP2018/031975 (dated Mar. 2020).
Office Action in Vietnamese Application No. 1-2020-01095 (dated May 2023).

* cited by examiner

|  | GAS | NUMBER OF UFB | CHANGE IN STAPHYLOCOCCUS AUREUS | CHANGE IN ESCHERICHIA COLI |
|---|---|---|---|---|
| TEST A | OZONE | 2.4 BILLION/ml | 1/1000 OR LESS | 1/1000 OR LESS |
| TEST B | NITROGEN | 1.2 BILLION/ml | 1/100 OR LESS | 1/100 OR LESS |
| TEST C | OZONE | 28.8 BILLION/ml | 1/1000 OR LESS | 1/1000 OR LESS |
| TEST D | NITROGEN | 2.4 BILLION/ml | 1/100 OR LESS | 1/100 OR LESS |
| TEST E | NITROGEN | 12.0 BILLION/ml | 1/100 OR LESS | 1/100 OR LESS |
| COMPARISON TARGET A | NONE | 0 | NONE | NONE |
| COMPARISON TARGET B | NONE | 0 | NONE | NONE |
| COMPARISON TARGET C | NONE | 0 | NONE | NONE |
| COMPARISON TARGET D | NONE | 0 | NONE | NONE |
| COMPARISON TARGET E | NONE | 0 | NONE | NONE |

FIG.19

ULTRAFINE BUBBLE GENERATING METHOD, ULTRAFINE BUBBLE-CONTAINING LIQUID MANUFACTURING APPARATUS AND MANUFACTURING METHOD, AND ULTRAFINE BUBBLE-CONTAINING LIQUID

TECHNICAL FIELD

The present invention relates to a generating method for generating ultrafine bubbles with a diameter of less than 1.0 μm, an ultrafine bubble-containing liquid manufacturing apparatus and manufacturing method, and an ultrafine bubble-containing liquid.

BACKGROUND ART

In recent years, techniques to apply the characteristics of fine bubbles such as microbubbles with a microscale diameter and nanobubbles with a nanoscale diameter have been developed. In particular, the benefit of ultrafine bubbles (hereinafter also referred to as "UFBs") with a diameter of less than 1.0 μm has been confirmed in various fields.

PTL 1 discloses an apparatus that generates fine bubbles by subjecting gas to pressure dissolution by means of a pressure dissolution method to generate pressurized liquid and emitting a jet of the pressurized liquid from a nozzle. PTL 2 discloses an apparatus that generates fine bubbles by repeating diversion and confluence of a liquid-gas mixture by means of a mixing unit.

CITATION LIST

Patent Literature

PTL 1: Japanese Patent No. 6118544
PTL 2: Japanese Patent No. 4456176

SUMMARY OF INVENTION

Technical Problem

In the apparatus disclosed in PTL 1, liquid should have a high pressure of 0.5 to 0.6 MPa. In the apparatus disclosed in PTL 2, liquid should have a high pressure of about 30 atm, and furthermore, complicated channels cause upsizing of the apparatus and an increase in power consumption. Accordingly, both the apparatuses disclosed in PTL 1 and PTL 2 have complicated configurations and are difficult to downsize.

Further, in either of the apparatuses disclosed in PTL 1 and PTL 2, at the time of UFB generation, a relatively large amount of millibubbles with a millimeter-scale diameter and microbubbles with a microscale diameter are generated in addition to UFBs with a nanoscale diameter. This makes it difficult to generate UFBs efficiently. In addition, in order to extract UFBs from bubbles of various sizes, a large container is necessary and the apparatus thus becomes more difficult to downsize.

An object of the present invention is to generate ultrafine bubbles efficiently with a simple configuration.

Solution to Problem

An ultrafine bubble generating method according to the present invention is characterized in that ultrafine bubbles are generated by causing film boiling.

Advantageous Effects of Invention

According to the present invention, ultrafine bubbles can be efficiently generated with a simple configuration by causing film boiling in liquid.

BRIEF DESCRIPTION OF DRAWINGS

FIG. 19 is a table illustrating the bactericidal effect of UFB-containing liquids as a thirteenth embodiment of the present invention;

DESCRIPTION OF EMBODIMENTS

Embodiments of the present invention will be described below with reference to the drawings.

First Embodiment

Figure 1:
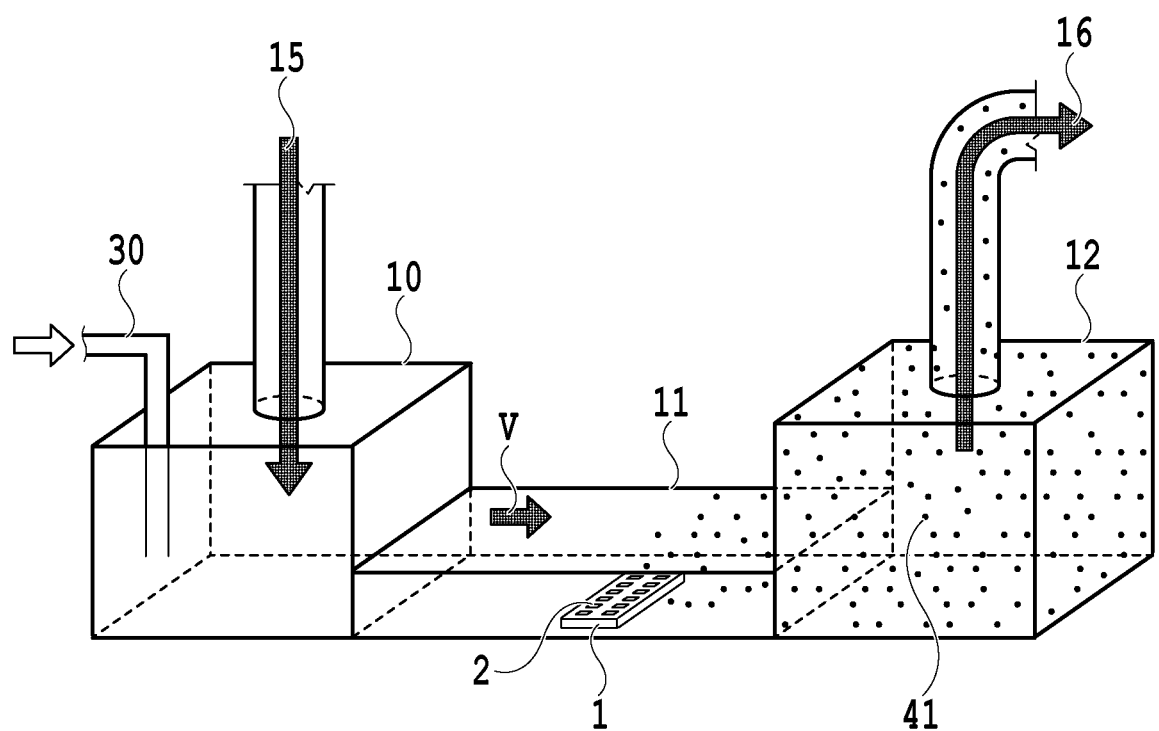
FIG. 1 is a schematic configuration diagram of a UFB-containing liquid manufacturing apparatus in a first embodiment of the present invention.

FIG. 1 is a schematic configuration diagram of a bubble generating apparatus in a first embodiment of the present invention as an example. The generating apparatus is incorporated into a bubble-containing liquid manufacturing apparatus. The apparatus of the present embodiment efficiently generates ultrafine bubbles (hereinafter also referred to as "UFBs") with a nanoscale diameter, namely, a diameter of less than 1.0 μm. A water flow channel 11, which is a liquid chamber, is formed between a water supply tank 10 and a water storage tank 12. Liquid is supplied from a water supply channel 15 to the water supply tank 10. The liquid flows out of the water supply tank 10 and then flows through the water flow channel 11 at a flow velocity V. The liquid is accumulated inside the water storage tank 12 and discharged from a discharge channel 16. The water flow channel 11, which is a liquid chamber storing liquid, is equipped with a substrate 1 having a heating resistance element (heater, electrothermal conversion element) 2 for heating liquid within a predetermined region of the water flow channel 11 and causing film boiling. As will be described later in detail, UFBs are generated in liquid by heating the liquid by means of the heating resistance element 2 and causing film boiling.

As a liquid, for example, pure water, ion exchange water, distilled water, bioactive water, magnetic water, lotion, tap water, seawater, river water, clean water and waste water, lake water, groundwater, and rainwater can be used. A liquid mixture including any of the above liquids and the like can also be used. Further, a mixed solvent of water and a water-soluble organic solvent can be used. A water-soluble organic solvent mixed with water for use is not particularly limited, but for example, the following can be specifically used: alkyl alcohols having 1 to 4 carbon atoms such as methyl alcohol, ethyl alcohol, n-propyl alcohol, isopropyl alcohol, n-butyl alcohol, sec-butyl alcohol, and tert-butyl alcohol; amides such as N-methyl-2-pyrrolidone, 2-pyrrolidone, 1,3-dimethyl-2-imidazolidinone, N,N-dimethylformamide, and N,N-dimethyl acetamide; ketones or ketoalcohols such as acetone and diacetone alcohol; cyclic ethers such as tetrahydrofuran and dioxane; glycols such as ethylene glycol, 1,2-propylene glycol, 1,3-propylene glycol, 1,2-butanediol, 1,3-butanediol, 1,4-butanediol, 1,5-pentanediol, 1,2- hexanediol, 1,6-hexanediol, 3-methyl-1, 5-pentanediol, diethylene glycol, triethylene glycol, and thiodiglycol; lower alkyl ethers of polyhydric alcohol such as ethylene glycol monomethyl ether, ethylene glycol monoethyl ether, ethylene glycol monobutyl ether, diethylene glycol monomethyl ether, diethylene glycol monoethyl ether, diethylene glycol monobutyl ether, triethylene glycol monomethyl ether, triethylene glycol monoethyl ether, and triethylene glycol monobutyl ether; polyalkylene glycols such as polyethylene glycol and polypropylene glycol; and triols such as glycerol, 1,2,6-hexanetriol, and trimethylolpropane. These water-soluble organic solvents may be used singly or in combination. As described above, various liquids in which film boiling can occur are applicable.

Figure 2A:
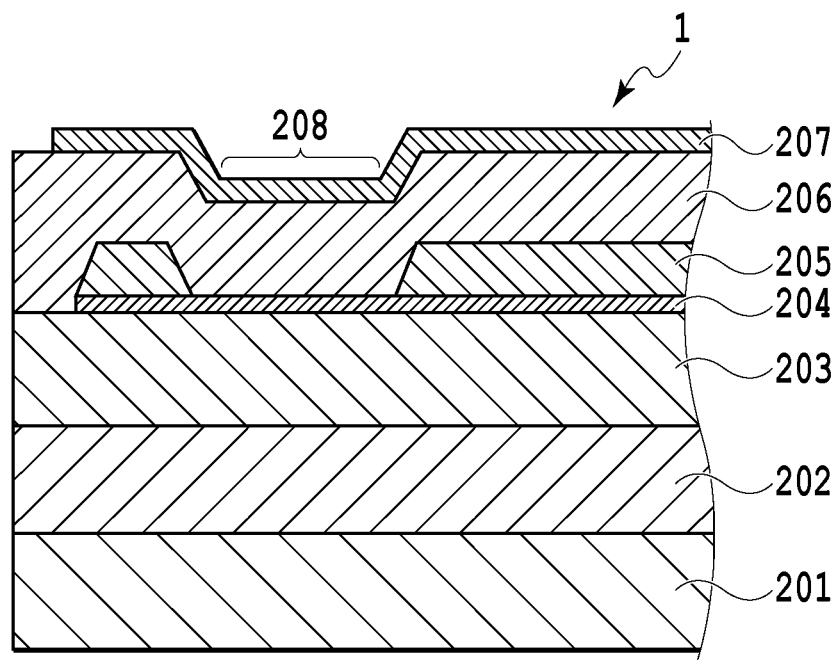
FIG. 2A is a cross-sectional view of a substrate in FIG. 1.

FIG. 2A is a cross-sectional view of the substrate (hereinafter also referred to as "element substrate") 1 having the heating resistance element as a heating portion, which is used in the apparatus of FIG. 1. In the element substrate 1 of the present embodiment, a thermal oxide film 202 as a heat storage layer and an interlayer film 203 also serving as a heat storage layer are laminated on a surface of a silicon substrate 201. As the interlayer film 203, an $SiO_2$ film or a SiN film can be used. On a surface of the interlayer film 203, a resistive layer 204 is formed. On a surface of the resistive layer 204, wiring 205 is partly formed. As the wiring 205, Al alloy wiring composed of Al, Al—Si, Al—Cu or the like can be used. On a surface of the wiring 205, resistive layer 204, and interlayer film 203, a protective layer 206 composed of an $SiO_2$ film or a $Si_3N_4$ film is formed. On a surface of the protective layer 206, an anti-cavitation film 207 is formed in and around a portion corresponding to a heat working unit 208 as a heating portion to protect the protective layer 206 against chemical and physical impacts caused by heating of the resistive layer 204. On the surface of the resistive layer 204, a region in which the wiring 205 is not formed is the heat working unit 208 in which the resistive layer 204 is heated. The heating portion of the resistive layer 204 in which the wiring 205 is not formed functions as a heating resistance element (heater) 2. In this manner, the layers in the element substrate 1 are successively formed on the surface of the silicon substrate 201 by a semiconductor manufacturing technique, thereby providing the silicon substrate 201 with the heat working unit 208. The illustrated configuration is an example and various other configurations are applicable. For example, a configuration in which the lamination order of the resistive layer 204 and the wiring 205 is reversed and a configuration in which an electrode is connected to the lower surface of the resistive layer 204 (a so-called plug electrode configuration) are applicable. In short, any configuration is applicable as long as the heat working unit 208 can heat liquid and cause film boiling in the liquid as described later.

Figure 2B:
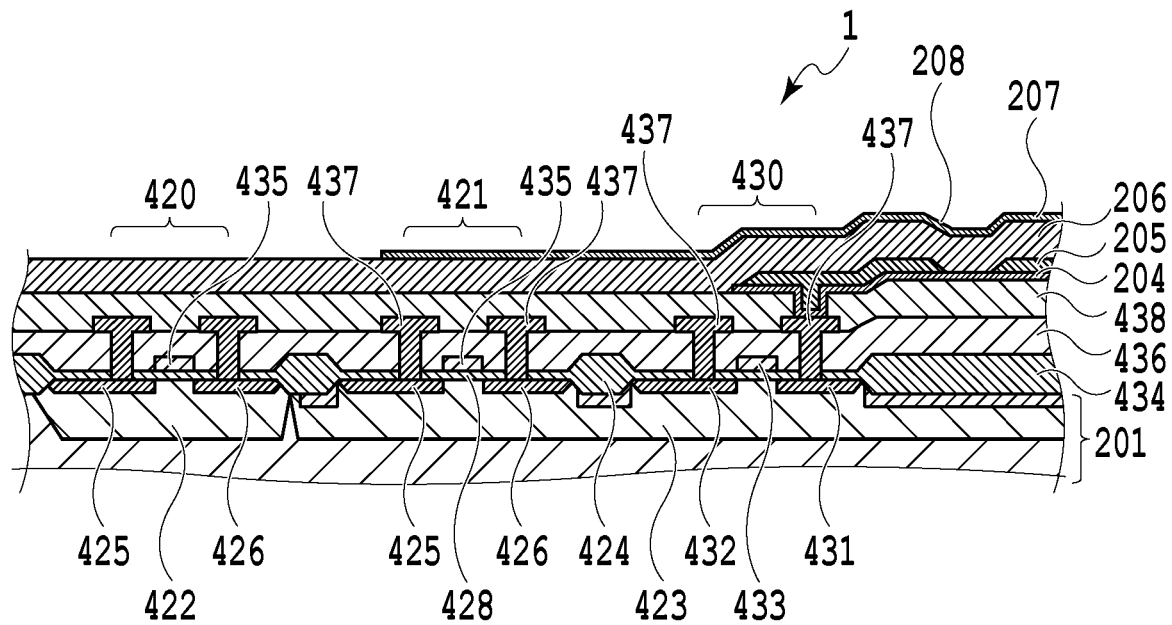
FIG. 2B is a cross-sectional view of the substrate in FIG. 1.

FIG. 2B shows an example of a cross-sectional view of a region of the element substrate 1 including a circuit connected to the wiring 205.

On a surface of the silicon substrate 201, which is a P-type conductor, an N-type well region 422 and a P-type well region 423 are partly formed. A P-MOS 420 is formed on the N-type well region 422 and an N-MOS 421 is formed on the P-type well region 423 by the steps of injection and diffusion of impurities such as ion implantation in a general MOS process. The P-MOS 420 includes a source region 425 and a drain region 426 which are obtained by partly injecting N-type or P-type impurities into a surface of the N-type well region 422, gate wiring 435, and the like. The gate wiring 435 is deposited on a surface of a portion of the N-type well region 422 excluding the source region 425 and the drain region 426 via a gate insulating film 428 having a thickness of several hundred Å. The N-MOS 421 includes the source region 425 and the drain region 426 which are obtained by partly injecting N-type or P-type impurities into a surface of the P-type type well region 423, the gate wiring 435, and the like. The gate wiring 435 is deposited on a surface of a portion of the P-type well region 423 excluding the source region 425 and the drain region 426 via the gate insulating film 428 having a thickness of several hundred Å. The gate wiring 435 is composed of polysilicon having a thickness of 4000 Å to 5000 Å and deposited by a CVD method. The P-MOS 420 and the N-MOS 421 form a C-MOS logic.

In a portion of the P-type well region 423 other than the N-MOS 421, a N-MOS transistor 430 is formed for driving the electrothermal conversion element (heating resistance element). The N-MOS transistor 430 includes a source region 432 and a drain region 431 which are partly formed on the surface of the P-type well region 423 by the steps of injection and diffusion of impurities and the like, gate wiring 433, and the like. The gate wiring 433 is deposited on a surface of a portion of the P-type well region 423 excluding the source region 432 and the drain region 431 via the gate insulating film 428.

In the present embodiment, the N-MOS transistor 430 is used as the transistor for driving the electrothermal conversion element. However, the transistor for driving may be any transistor as long as it has the capability of driving a plurality of electrothermal conversion elements separately and can obtain a fine structure as described above, and is not limited to the N-MOS transistor 430. In addition, although the electrothermal conversion element and the transistor for driving it are formed on the same substrate in the present embodiment, they may be formed on different substrates.

Between adjacent elements, for example, between the P-MOS 420 and N-MOS 421 and between the N-MOS 421 and N-MOS transistor 430, oxide film isolation regions 424 are formed by field oxidation of a thickness of 5000 Å to 10000 Å. The elements are isolated by the oxide film isolation regions 424. In the oxide film isolation regions 424, a portion corresponding to the heat working unit 208 functions as a first heat storage layer 434 on the silicon substrate 201.

On a surface of each of the elements, namely the P-MOS 420, N-MOS 421, and N-MOS transistor 430, an interlayer insulating film 436 is formed by the CVD method, the interlayer insulating film 436 being composed of a PSG film, a BPSG film or the like having a thickness of about 7000 Å. After the interlayer insulating film 436 is planarized by heat treatment, Al electrodes 437 to be a first wiring layer are formed via contact holes penetrating the interlayer insulating film 436 and the gate insulating film 428. On surfaces of the interlayer insulating film 436 and Al electrodes 437, an interlayer insulating film 438 is formed by a plasma CVD method, the interlayer insulating film 438 being composed of an $SiO_2$ film having a thickness of 10000 Å to 15000 Å. On portions of a surface of the interlayer insulating film 438 corresponding to the heat working unit 208 and N-MOS transistor 430, the resistive layer 204 is formed by a co-sputtering method, the resistive layer 204 being composed of a TaSiN film having a thickness of about 500 Å. The resistive layer 204 is electrically connected to the Al electrode 437 near the drain region 431 via a through-hole formed in the interlayer insulating film 438. On the surface of the resistive layer 204, the Al wiring 205 is formed as a second wiring layer to be wiring connecting with each electrothermal conversion element. The protective layer 206 on surfaces of the wiring 205, resistive layer 204, and interlayer insulating film 438 is composed of a SiN film formed by the plasma CVD method and having a thickness of 3000 Å. The anti-cavitation film 207 deposited on a surface of the protective layer 206 is composed of a thin film of at least one metal selected from Ta, Fe, Ni, Cr, Ge, Ru, Zr, Ir, and the like, having a thickness of about 2000 Å. As the resistive layer 204, any material capable of causing film boiling in liquid such as TaN0.8, CrSiN, TaAl, or WSiN is applicable in addition to TaSiN described above.

Figure 3:
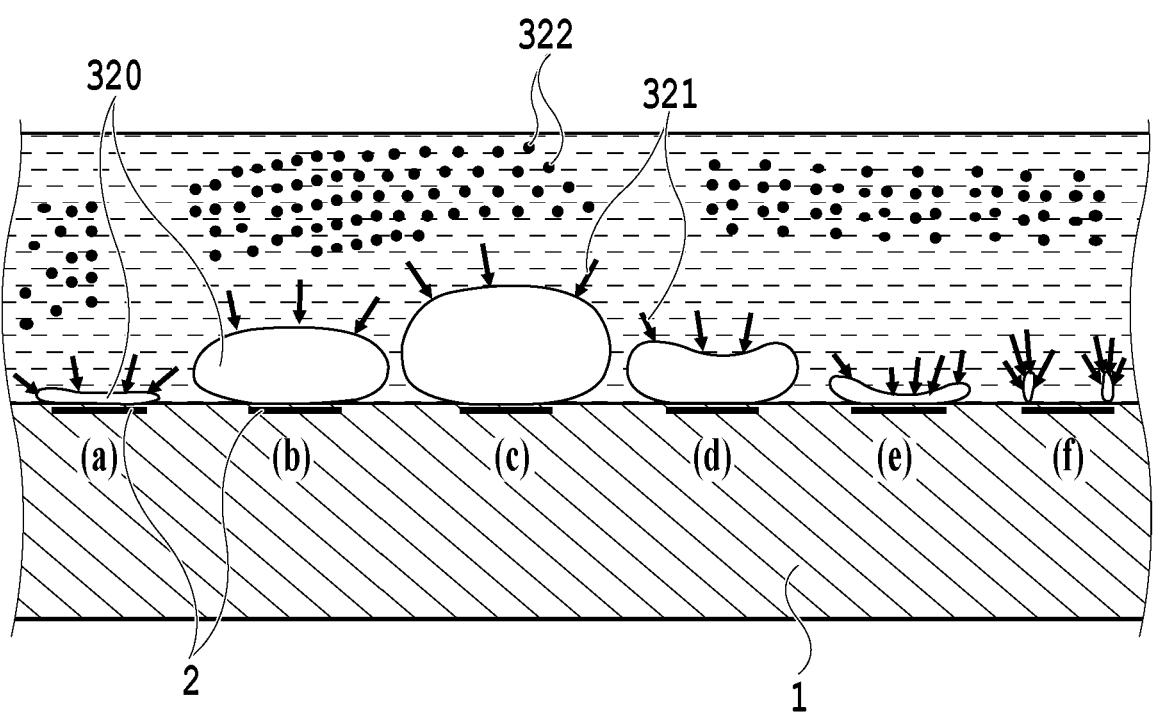
FIG. 3 is a diagram illustrating a UFB generation mechanism in the first embodiment of the present invention.

FIG. 3 is a diagram illustrating a mechanism of generation of a UFB 41 by means of the apparatus shown in FIG. 1. FIG. 3 shows six stages (a) to (f) for each elapsed time. FIG. 3 schematically shows six heating resistance elements 2 arranged side by side to facilitate explanation.

As described above, the heating resistance element (heater) 2 is formed on the substrate 1. The heater 2 is connected to the electrical wiring 205 (FIG. 2A) and supplied with constant power by a pulse signal. A pulse width of the pulse signal is about 0.5 µsec to 10.0 µsec. A voltage is applied to the heater 2 in only an extremely short time and an extremely high heat flux is provided for the heater 2. In a case where a surface temperature of the heater 2 goes close to about 300° C., a phenomenon that appears to be nucleate boiling is observed on the surface of the heater 2 at an extremely initial stage (about several picoseconds), it immediately exceeds transition boiling, and a bubble 320 is generated by film boiling after sub-microseconds to several microseconds as shown in the stage (a) of FIG. 3. After that, the bubble 320 transitions to its growth stage as shown in the stage (b) of FIG. 3. An initial bubbling pressure at this time can be predicted by simulation. As a result of calculation by commercially available fluid-based software using the VOF method (such as Fluent [available from ANSYS, Inc.] or FLOW-3D [available from Flow Science, Inc.]), the bubbling pressure was about 8 to 10 MPa, which are close to values of saturation vapor pressure of water.

Further, since the power is continuously supplied to the heater 2 covered with the bubble 320, the surface temperature of the heater 2 further increases up to about 600 to 800° C. However, the power supply to the heater 2 is stopped at an initial stage of the growth process of the bubble 320. After the bubble 320 grows to a maximum bubble with a maximum diameter (about several times the area of the heater) as shown in the stage (c) of FIG. 3, the bubble 320 transitions to its elimination process by negative pressure inside the bubble 320 as shown in the stage (d) of FIG. 3. Near the end of the bubble elimination process, a phenomenon of cavitation I occurs, where liquid contacts the surface of the heater 2 again as shown in the stage (e) of FIG. 3. The main cavitation I at this stage is caused by re-contact of liquid with the surface of the heater 2 at the central part of the bubble viewed from above. At this time, the surface temperature of the heater 2 decreases to about 100° C. or less (the surface temperature of the heater 2 at this time differs according to a design and film configuration of the heater layer). Then, as shown in the stage (f) of FIG. 3, the bubble is eliminated in at least one extremely small region on the surface of the heater 2, and at this time, spark-like cavitation II occurs. Depending on the circumstances, as shown in the stage (f) of FIG. 3, the bubble is divided into a plurality of bubbles at a shrinkage process of the bubble and each of the bubbles is eliminated, with the result that cavitation II occurs in different positions on the surface of the heater 2.

The mechanical impact forces of the cavitation I and the cavitation II may each have a numerical value roughly equal to or greater than the initial bubbling pressure of film boiling. As a result of measurement using the aforementioned commercially available software or the like, the pressure by the cavitation I was about 5 to 20 MPa. That is, in a case where the heater 2 has a size of 20 µm×20 µm, a pressure applied to the heater 2 per unit area is 0.02 MPa/µm$^2$. On the other hand, a pressure per unit area by the cavitation II, which occurrs in a region of about 1.0 is 5 to 20 MPa/µm$^2$. In short, an impact pressure per unit area at the time of film boiling reaches its peak at the occurrence of the cavitation II. Although a visualization experiment on UFBs 322 with a diameter of 100 to 150 nm is difficult and their generation mechanism cannot be determined, it is presumed that UFBs 322 are generated from gas 321 dissolved in the liquid at the stages (a) through (f) of FIG. 3. More specifically, it is presumed that the pressure by cavitation causes the dissolved gas 321 (particles) dissolved in the liquid to sublime, whereby UFBs are generated. It is therefore presumed that more UFBs are generated at the initial bubbling stage (a) with high pressure, the stage (e) where the cavitation I occurs, and the stage (f) where the cavitation II occurs.

It is known as the principle of pressure dissolution and the like that gas dissolved in liquid is turned into bubbles by pressure applied to the liquid, temperature variations and the like. However, UFBs in the present embodiments are generated by film boiling in an extremely short time caused by driving a heater and they are different from the bubbles generated by the conventional method. In general, microscale microbubbles can be observed by means of an optical microscope, a high speed camera or the like. Generated microbubbles are eliminated several microseconds after their growth process. In contrast, bubbles with a nanoscale diameter (UFBs) have been conventionally difficult to observe because they are too small to be resolved by an optical microscope. However, the present inventors have confirmed the existence of UFBs through measurements using light scattering techniques and the like.

As a system for causing film boiling in liquid, various systems can be adopted. For example, a configuration in which film boiling is caused by the heater 2 provided in midair in a space where liquid exists or a configuration in which the direction of growth of bubbles is opposite to the direction of movement of liquid accompanying the growth of the bubbles can be adopted. As a UFB generating method, the configuration of the element substrate 1 and the configuration of the generating apparatus described above are just examples. UFBs can be generated by heating the heating resistance element 2 to about 300° C. or more in liquid and forming bubbles in the liquid. That is, UFBs can be generated by forming bubbles in liquid by using film boiling and it is presumed that UFBs are generated at least at the stage (a) in FIG. 3. For example, bubbles formed by film boiling at the stage (a) of FIG. 3 may communicate with the atmosphere in a process of the subsequent stages (b) to (f), whereby the process of the stage (f), which is the bubble elimination process, may be omitted. As described above, UFBs with a diameter of less than 1.0 µm can be generated by forming bubbles in liquid using film boiling. At this time, microbubbles with a microscale diameter and nanobubbles with a nanoscale diameter are hardly generated. That is, only UFBs can be substantially generated with high efficiency.

Further, instead of the configuration in which liquid flows through a region where the heating resistance element 2 is provided as shown in FIG. 1, bubbles may be generated by film boiling while liquid remains at rest.

Incidentally, regarding UFBs, research is now conducted by the ISO/TC 281, which has its office in Japan, to standardize and to clarify stabilization mechanisms. Bubbles of 1.0 μm or less have been defined as the standard for UFBs at the ISO/TC 281 conference held at the end of 2017. However, a mechanism of long-term and stable existence of UFBs of 1.0 μm or less in a solution is not yet clarified. To clarify the mechanism, various institute in the world are currently making experimental observations and theoretical calculations. In short, regarding those invisible bubbles (UFBs), there still remain a lot of phenomena to be clarified. Under the circumstances, the inventors of the present invention presume two mechanisms (second and third mechanisms) in addition to the aforementioned UFB generation mechanism (first mechanism).

Figure 23:
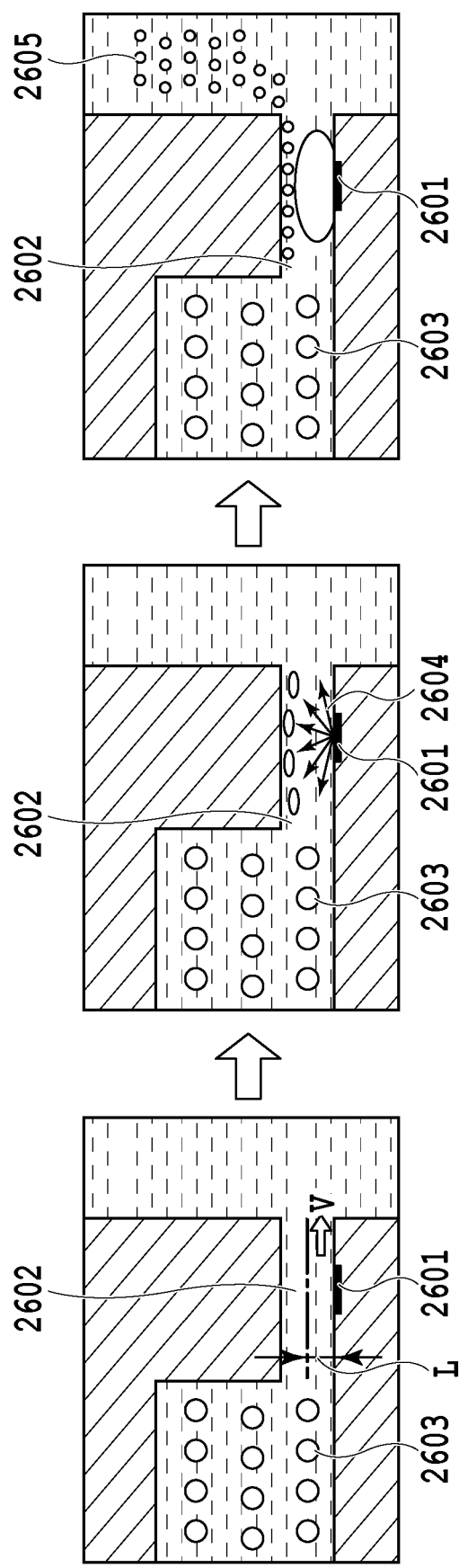
FIG. 23 is a diagram illustrating a UFB generation mechanism in the first embodiment of the present invention.

FIG. 23 shows the UFB generation mechanism (second mechanism) using the apparatus of FIG. 1. A flow of liquid (about 10 m/s) is generated in a channel 2602 filled with tap water. Microbubbles 2603 of 1.0 μm or more containing gas therein are blown into the flow. A short pulse of square wave is applied to a heater 2601 provided in the channel 2602, whereby shock waves 2604 are propagated through the liquid inside the channel 2602. At this time, a shear strength (∝ V/L) occurs between a channel wall (zero velocity) and the circulation flow inside the channel 2602. V indicates a flow rate and L indicates a channel width (a distance from the channel wall to the center of the channel). In a case where the flow rate V is 10 m/s, a 10E(+6)-order shear strength occurs inside the channel having a channel width L of about several tens micrometers. An impact pressure at the occurrence of film boiling by driving the heater 2601 is about 10 [MPa].

From the above, the inventors of the present invention presume, as the UFB generation mechanism (second mechanism) of the present invention, that the shock waves generated by driving the heater 2601 split the microbubbles 2603 inside the channel 2602 into UFBs 2605.

Next, the UFB generation mechanism (third mechanism) using the apparatus of FIG. 1 is described. A surface of the heater is rapidly heated by applying a short pulse of square wave to the heater. At this time, liquid near the heater partly evaporates into vapor bubbles. The vapor bubbles are partly left inside the liquid as fine vapor bubbles (UFBs) irrespective of a film boiling phenomenon. They are turned into UFBs and stay in the liquid for a long period. Further, it is assumed that the processes of bubble growth and bubble shrinkage in a film boiling phenomenon includes a departure process of fine bubbles from surfaces of bubbles (microbubbles) changing their shapes. The fine bubbles (UFBs) departed at that time are presumed to be left inside the liquid. From the above view point, the inventors of the present invention presume, as the UFB generation mechanism (third mechanism) of the present invention, that vapor bubbles generated at the time of heating the heater and the fine bubbles generated in the film boiling process are turned into UFBs and left inside the liquid.

It is also considered that two or three of the above three mechanisms (first to third mechanisms) function to generate UFBs.

Next, the properties of UFBs will be described. For convenience of explanation, it is assumed that UFBs are formed in an aqueous solution (such as pure water).

UFBs commercially available at present have a diameter of 50 to 500 nm (at the ISO/TC 281 conference held at the end of 2017, UFBs have been defined as bubbles of 1.0 μm or less). Such fine bubbles have a surface potential dependent on pH in an aqueous solution as a physical property. This is because a hydrogen-bond network of water at a bubble interface requires more hydrogen ions or hydroxide ions as its constituent factors. Since charge of bubbles keeps an equilibrium condition with respect to the surrounding water, it has a constant value irrespective of bubble diameters. Further, since an electrically charged bubble surface exerts an electrostatic force, ions having charge opposite to the bubble charge are attracted toward a gas-liquid interface. Although the bubble charge is kept in equilibrium, in a case where the bubble is downsized in a short time, the charge is concentrated. In a case where the speed of bubble downsizing is accelerated and the bubble diameter is reduced, the amount of charge per unit area increases in inverse proportion to the square of the bubble diameter.

Since a fine bubble such as a UFB is surrounded by its gas-liquid interface, the inside of the bubble is pressurized by itself under the influence of surface tension. A pressure rise inside the bubble with respect to environmental pressure is logically estimated as follows based on the Young-Laplace equation:

$$\Delta P = 4\sigma/D \quad (1)$$

In the above equation, $\Delta P$ is the degree of a pressure rise, $\sigma$ is the surface tension, and D is a bubble diameter. In the case of distilled water at room temperature, a pressure rise in a bubble with a diameter of 10 μm is about 0.3 atm and a pressure rise in a bubble with a diameter of 1 μm is about 3 atm. Gas inside a bubble pressurized by itself dissolves into water by the Henry's law. Accordingly, a diameter of the bubble gradually decreases, which accompanies a rise in pressure inside the bubble, thereby accelerating the speed of the decrease in bubble diameter. As a result, a UFB with a diameter of 1 μm or less is completely dissolved almost in an instant. In other words, a UFB exists only extremely instantaneously.

In actuality, however, it is presumed that a UFB exists stably through the following mechanism.

That is, in the case of a UFB, since the charge is concentrated in a very high density at its gas-liquid interface, the UFB is prevented from shrinking by an electrostatic repulsion that acts between the opposite charges at its ball-like gas-liquid interface. Further, the concentrated high electric field acts to generate, around the UFB, an inorganic shell mainly composed of electrolyte ions such as iron ions, which prevents dissipation of the gas inside the UFB. Such a shell, differently from a surfactant or organic shell, easily collapses itself due to deviation of charge around the UFB caused by contact of the UFB with other substances such as bacteria. In the case of the collapse of the shell, the gas inside the UFB is easily released to an aqueous solution.

In general, forces that act on a bubble in liquid include buoyancy and drag. Buoyancy is proportional to the volume of a bubble (proportional to the cube of the radius of the bubble). Drag is proportional to the cross-sectional area of a bubble (proportional to the square of the radius of the bubble) and proportional to the square of the rising speed of the bubble. More specifically, in a case where the radius of a bubble is denoted by r, the density of water is denoted by $\rho$, the gravitational acceleration is denoted by g, the viscosity of water is denoted by $\eta$, and the speed of bubble movement is denoted by u, buoyancy that acts on the bubble (the density of the bubble is ignored) is expressed by the following equation (2) based on the Archimedes' principle:

$$F = 4\pi r^3 \rho g / 3 \quad (2)$$

Drag that acts on the bubble is expressed by the following equation (3) based on the Stokes' law:

$$F = 6\pi \eta r u \quad (3)$$

According to the above equations (2) and (3), the speed of bubble movement u is expressed by the following equation (4):

$$u=(2/9)r^2\pi g/\eta \quad (4)$$

From the equation (4), it is understood that the speed of bubble movement u increases as the radius r of the bubble becomes larger. Accordingly, for example, in the case of a bubble with a milliscale diameter, buoyancy exerted on the bubble and a rising speed of the bubble are high since the radius of the bubble is large.

In a case where the radius r of the bubble under 1 atm is denoted by a, the radius r and the depth of water h are expressed by the following equation (5):

$$R=a\times\{101325/(\pi gh+101325)\}^{1/3} \quad (5)$$

From the equations (4) and (5), it is understood that the rising speed of the bubble increase as the depth of water decreases.

It is assumed that the solubility of UFBs with a diameter of less than 1.0 μm is reduced by a salting-out phenomenon and the UFBs thus exist in liquid stably for a long period. In other words, on the assumption that UFBs exist stably for a long period due to a salting-out phenomenon, a UFB water with a pH close to 7 cannot exist. However, there is a case where UFBs exist stably even in a neutral liquid.

The solubility of UFBs with a diameter of less than 1.0 μm is reduced by a salting-out phenomenon and the UFBs thus exist in liquid stably for a long period. In general, in a state where UFBs and larger bubbles are mixed, the UFBs float up under the influence of the larger bubbles or are affected by cavitation destruction due to external pressure, with the result that the UFBs have a short life. However, according to the present invention, since large bubbles with a diameter of 1.0 μm or more are hardly generated in the case of generating UFBs, the life of the generated UFBs can get longer.

Figure 4A:
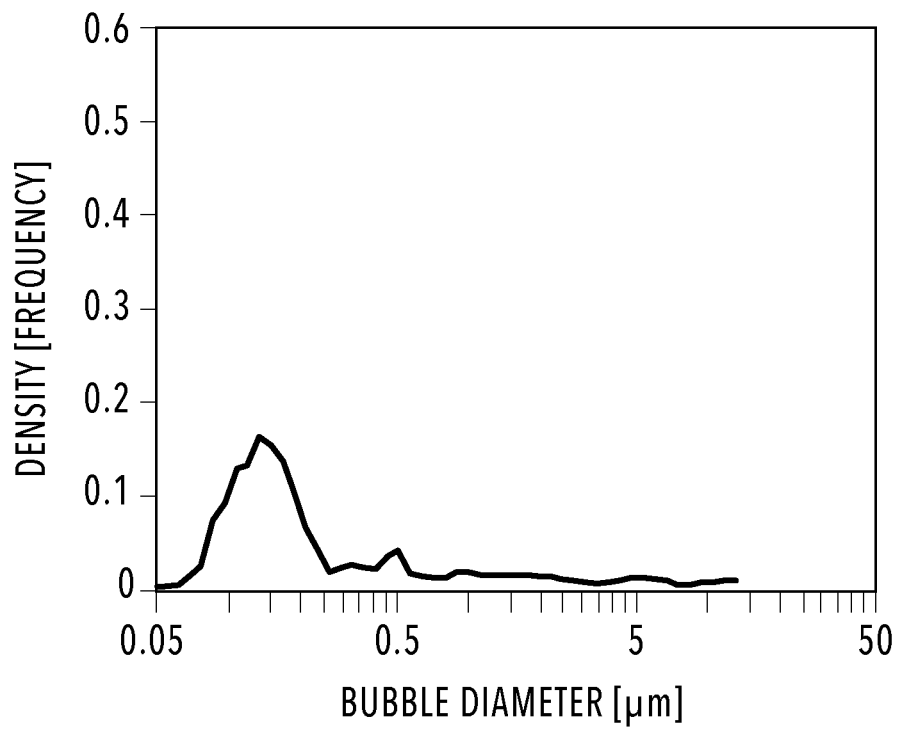
FIG. 4A is a graph illustrating a frequency distribution of bubble diameter in a UFB-containing liquid manufactured in the first embodiment of the present invention.

To be more specific, an electrical signal of a short pulse (1.0 μsec) of square wave was applied to the heater 2 to cause film boiling intermittently and repeatedly in industrial pure water. The electrical signal of square wave was applied to the heater 2 repeatedly 1.0e8 (1.0×10$^8$) times in a driving cycle of 100 μsec to cause a film boiling phenomenon and then the pure water was collected. The collected pure water was colorless and transparent, not whitish. The transparency was 1.0 mm or more. The collected pure water was set in a measurement device SALD-7500 (available from Shimadzu Corp.). As a result of measurement, a number density of UFBs with a diameter of less than 1.0 μm in the pure water was 1.0 billion per ml. A frequency distribution of bubble diameter at that time is shown in FIG. 4A. The number of UFBs with a diameter ranging from 10 nm to 400 nm was 99% of the whole. In the industrial pure water (raw water) before the occurrence of film boiling, a number density of UFBs was zero per ml.

FIG. 4A shows a measurement result 24 hours after the generation of UFBs, where the number of bubbles with a diameter of 1.0 μm or more was 0.006% of the whole. That is, UFBs with a diameter of less than 1.0 μm occupied 99.994% of the whole. Accordingly, the UFBs were hardly affected by the large bubbles with a diameter of 1.0 μm or more. Even after storage of such pure water containing UFBs in a glass container in a cool, dark place (about 25° C.) for three months, the number of UFBs remained virtually unchanged.

Bubbles 320 (microbubbles and millibubbles) generated by a film boiling phenomenon on the surface of the heater 2 are eliminated within several microseconds to several milliseconds since the inside of them has negative pressure. However, it was shown that numerous UFBs 322 were generated at the stages (a) through (f) in FIG. 3 including the film boiling through cavitation. A time required for the generation was about a little less than three hours. The number of UFBs 322 generated in one series of steps from film boiling through cavitation (stages [a] through [f]) was about 10.

UFBs 41 were generated by means of the apparatus of FIG. 1. 10,000 heaters 2 were provided on the substrate 1 and a pulse signal (pulse width: 1.0 μs, voltage: 24V) was applied to the heaters 2 at a driving frequency of 10 kHz. At that time, industrial pure water was supplied so that a flow velocity V in the water flow channel 11 was 1.0 L/h. As shown in FIG. 1, the substrate 1 was provided on the bottom of the water flow channel 11 to direct the heaters 2 above. Accordingly, the UFBs 41 generated along with film boiling of the pure water were dispersed upward inside the water flow channel 11 and contained in the pure water. The pure water containing the UFBs 41 flowed in directions shown by the arrow in FIG. 1 along the flow of pure water.

$$\text{Total Number of Heaters} = 1.0e4 (=1.0\times 10^4)$$

Number of *UFBs* Generated =

$$(1.0e4)\times 10\times (1.0e4)\times 60[s]\times 60[\min] = 3.6e12((UFBs/L)/h)$$

Figure 4B:
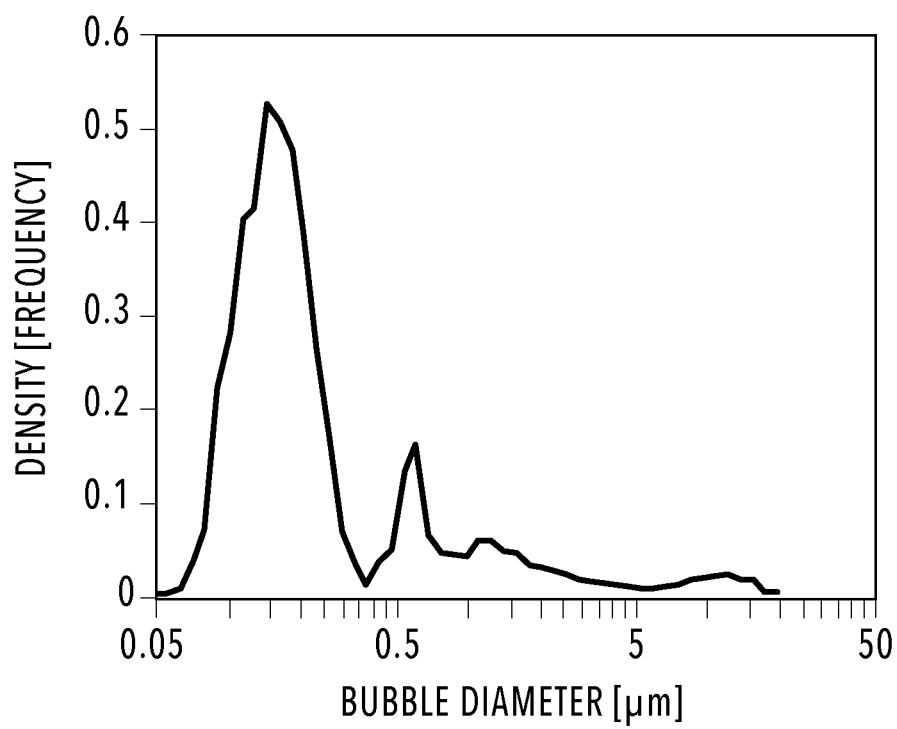
FIG. 4B is a graph illustrating a frequency distribution of bubble diameter in the UFB-containing liquid manufactured in the first embodiment of the present invention.

3.6 billion UFBs 41 per ml were generated in one hour. The UFBs 41 were thus generated in a high number density within a short time. To confirm that, the collected pure water was set in the measurement device SALD-7500 (available from Shimadzu Corp.). As a result of measurement, a number density of UFBs 41 with a diameter of less than 1.0 μm in the pure water was about 3.6 billion per ml. A frequency distribution of bubble diameter at that time is shown in FIG. 4B. The number of UFBs 41 with a diameter ranging from 10 nm to 400 nm was 99.8% of the whole.

Gas contained in the UFBs generated in the above manner was analyzed by the gas chromatography (GC-TCD) method. As a result of detection using He as a carrier gas, nitrogen gas and oxygen gas were detected. Further, as a result of measurement using Ar gas as a carrier gas, no hydrogen gas was detected. These results showed that the UFBs were generated from the air dissolved in the pure water at the stages (a) through (f) in FIG. 3 including film boiling through cavitation. In addition, a measurement device (NS-300 available from NanoSight Ltd.) was used to measure a zeta potential of UFBs in pure water (pH≈7.0) containing the UFBs. As a result of the measurement, although varied according to respective UFBs, the zeta potential had an average value of −46 mV (−10 to 150 mV).

Modification of First Embodiment

Figure 22:
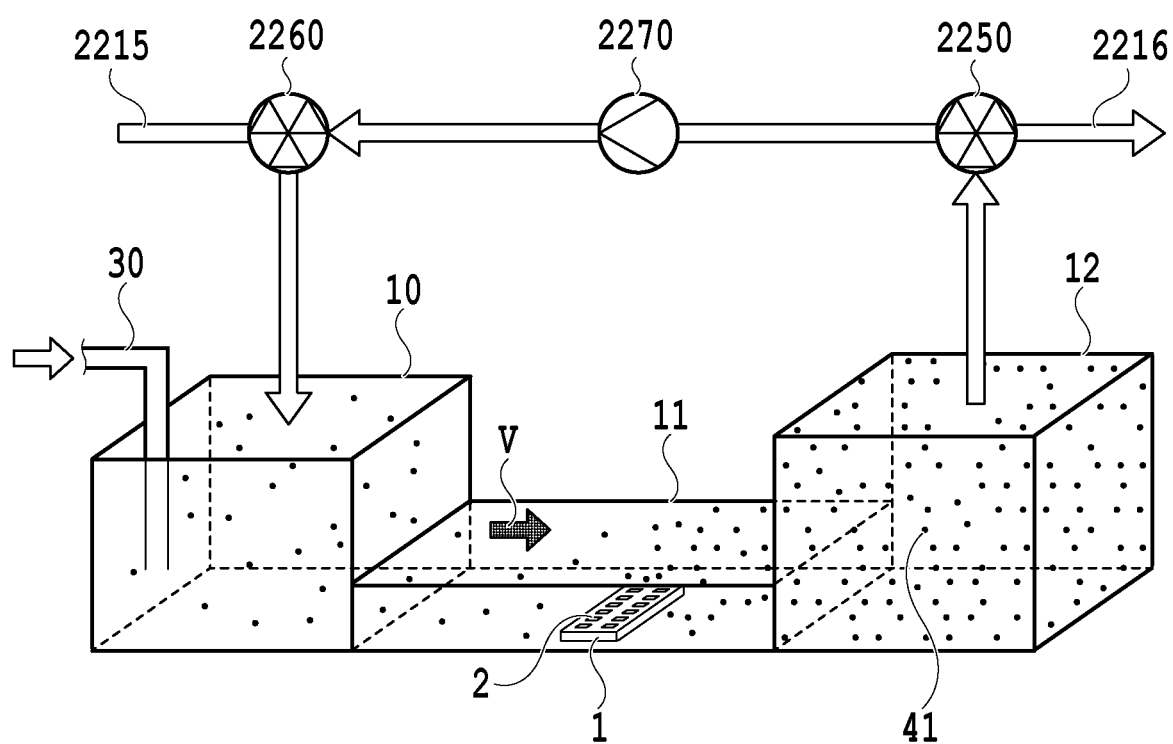
FIG. 22 is a diagram illustrating a UFB-containing liquid manufacturing apparatus as a modification of the first embodiment of the present invention.

FIG. 22 shows an apparatus based on the UFB generating apparatus shown in FIG. 1. The apparatus of FIG. 22 generates UFBs in a higher number density. In addition to the configuration of FIG. 1, this modification has a configuration in which liquid containing generated UFBs is circulated to generate UFBs again.

Liquid containing UFBs generated by causing film boiling by means of the heater 2 is returned to the supply container 10 via three-way valves 2250 and 2260 (circulation system), whereby UFBs can be generated again by causing film boiling by means of the heater 2. As a source of power to generate the circulation flow, a pump 2270 is connected to the circulation channel system. This configuration enables UFB generation in a high number density. A UFB-containing liquid (ultrafine bubble-containing liquid) of a desired number density can be generated by setting the number of liquid circulations and the flow rate of circulated liquid as appropriate. While the circulation flow is generated, a desired gas may be supplied continuously or intermittently from a gas injection port 30. In the case of generating nanobubbles of air, dissolution of the air may be facilitated by exposing the supply container 10 to the atmosphere and bringing liquid inside the supply container 10 into contact with the outside air.

Second Embodiment

Figure 5A:
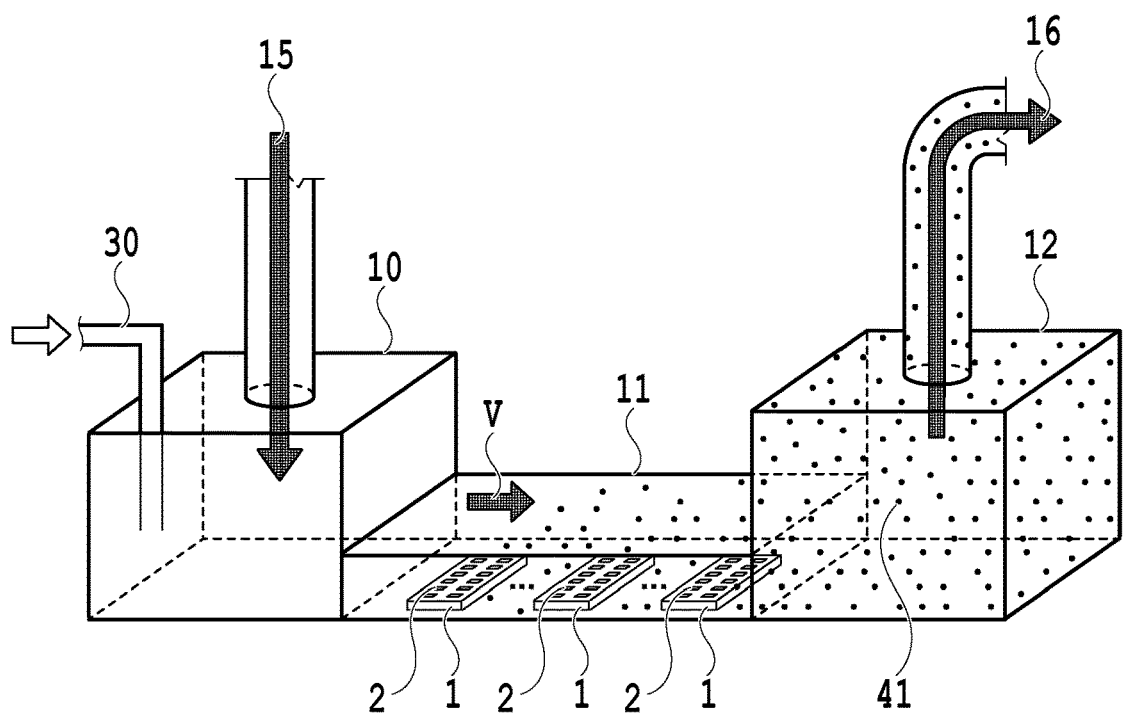
FIG. 5A is a diagram illustrating a UFB-containing liquid manufacturing apparatus in a second embodiment of the present invention.

FIG. 5A is a schematic configuration diagram of a bubble generating apparatus in a second embodiment of the present invention. The generating apparatus is incorporated into a bubble-containing liquid manufacturing apparatus. In the present embodiment, 10,000 heaters 2 were provided on one substrate 1 as in the first embodiment, and ten substrates 1 in total were mounted in series (only three substrates 1 are illustrated for simplification). To the heaters 2, a pulse signal (pulse width: 1.0 μs, voltage: 24V) was applied at a driving frequency of 20 kHz. Tap water was supplied to the water flow channel 11 and its flow velocity V was set at 1.0 L/h.

$$\text{Total Number of Heaters} = 1.0e4 \times 10 = 1.0e5 (= 1.0 \times 10^5)$$

Number of *UFBs* Generated =

$$(1.0e5) \times 10 \times (2.0e4) \times 60[s] = 1.2e12 ((\textit{UFBs}/\text{L}) / \min)$$

Figure 5B:
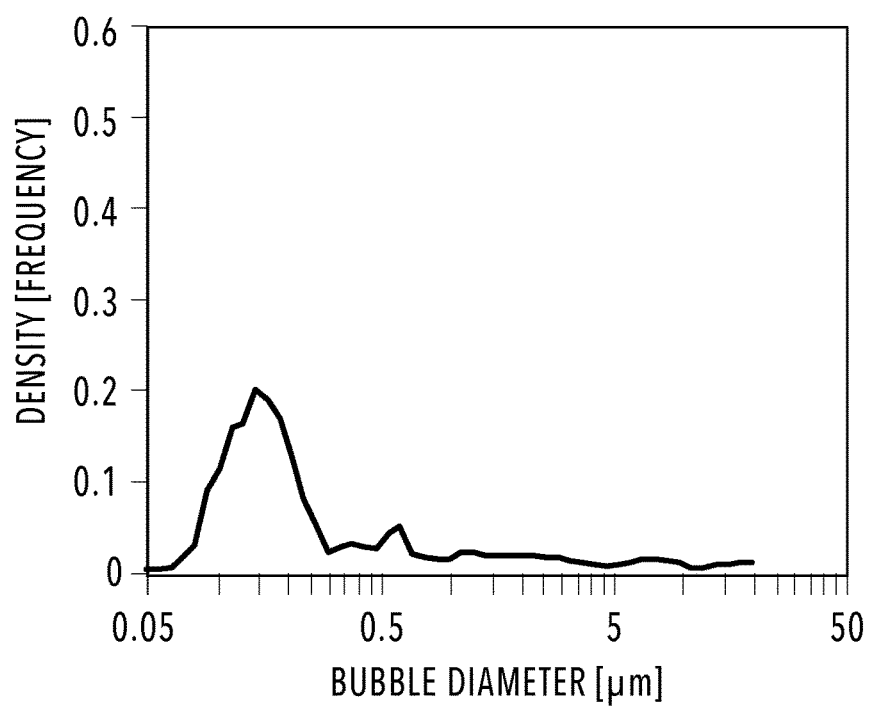
FIG. 5B is a graph illustrating the UFB-containing liquid manufacturing apparatus in the second embodiment of the present invention.

1.2 billion UFBs 41 per ml were generated in one minute. The UFBs 41 were thus generated in a high number density within an extremely short time. To confirm that, the collected tap water was set in the measurement device SALD-7500 (available from Shimadzu Corp.). As a result of measurement, a number density of UFBs 41 with a diameter of less than 1.0 μm in the tap water was about 1.2 billion per ml. A frequency distribution of bubble diameter at that time is shown in FIG. 5B. The number of UFBs 41 with a diameter ranging from 10 nm to 400 nm was 99.7% of the whole. Gas contained in the UFBs generated in the above manner was analyzed by the GC-TCD method as in the first embodiment. As a result of the analysis, nitrogen and oxygen were detected. The components of the tap water were also analyzed. As a result of the analysis, no increase in impurities was detected. It should be noted that the substrates 1 may be arranged in parallel, not in series, and may be arranged two-dimensionally.

As described above, according to the present invention, large bubbles with a diameter of 1.0 μm or more are hardly generated at the time of UFB generation. Accordingly, UFBs can be efficiently generated while saving space by providing a plurality of heaters 2 as UFB generation means and providing a plurality of substrates 1.

Third Embodiment

In a third embodiment, UFBs 41 were generated by means of the apparatus shown in FIG. 5A as in the second embodiment. The number of heaters 2 provided on each substrate 1, the number of substrates 1 mounted, the condition for driving the heaters 2, and the flow velocity V of tap water are the same as those in the second embodiment. However, in the third embodiment, nitrogen gas was injected from the gas injection port 30 into the tap water inside the water supply tank 10 for 24 hours to make the tap water bubble, thereby converting most of the gas dissolved in the tap water inside the water supply tank 10 into nitrogen gas. That is, the UFBs were generated by causing film boiling in the liquid in which the nitrogen gas was mainly dissolved.

Figure 6:
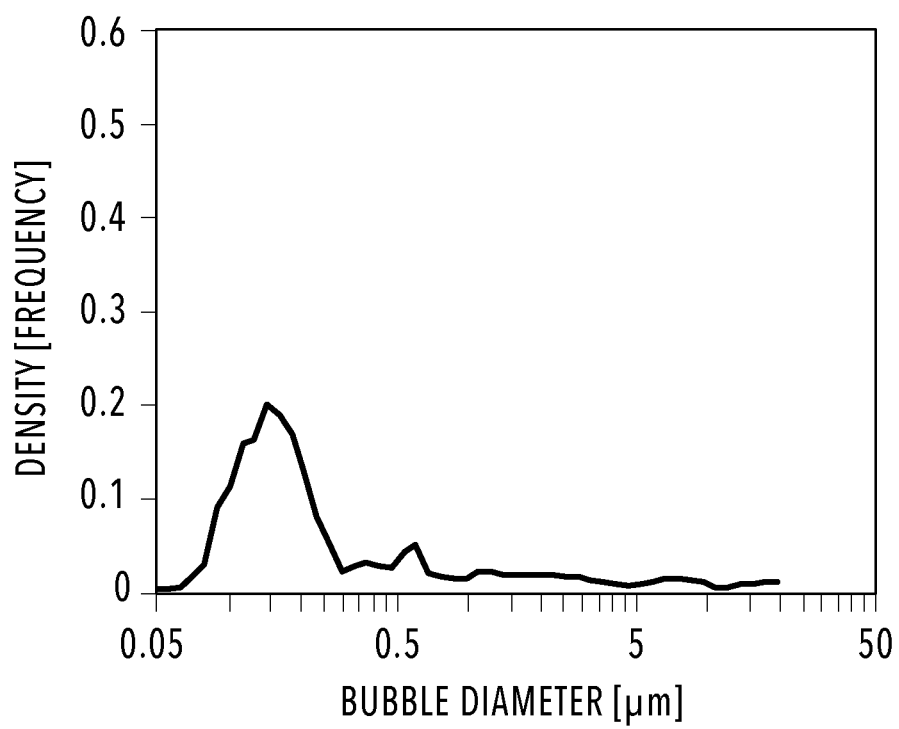
FIG. 6 is a graph illustrating a frequency distribution of bubble diameter in a UFB-containing liquid manufactured in a third embodiment of the present invention.

As in the second embodiment, 1.2 billion UFBs 41 per ml were generated in one minute. The UFBs 41 were thus generated in a high number density within an extremely short time. To confirm that, the collected tap water was set in the measurement device SALD-7500 (available from Shimadzu Corp.). As a result of measurement, a number density of UFBs 41 with a diameter of less than 1.0 μm in the tap water was about 1.2 billion per ml. A frequency distribution of bubble diameter at that time is shown in FIG. 6. The number of UFBs 41 with a diameter ranging from 10 nm to 400 nm was 99.0% of the whole. Gas contained in the UFBs generated in the above manner was analyzed by the GC-TCD method as in the second embodiment. As a result of the analysis, nitrogen and oxygen were detected and the amount of nitrogen was two to three times larger than that detected in the second embodiment. The components of the tap water was also analyzed. As a result of the analysis, no increase in impurities was detected. In the present embodiment, nitrogen gas had been injected into the liquid in advance. However, the present invention is not limited to this. Nitrogen gas may be injected into flowing liquid upstream of the heaters 2. Further, a gas to be injected is not limited to nitrogen gas.

The configuration of FIG. 22 shown as the modification of the first embodiment is also applicable to the second and third embodiments described above. For example, in a case where UFBs are generated by means of the plurality of substrates 1 as in the second embodiment and then resultant liquid is returned to the supply container 2210 by the circulation configuration shown in FIG. 22, UFBs can be generated again by means of the substrates 1. This enables more efficient generation of a UFB-containing liquid of a high number density.

Fourth Embodiment

Figure 7A:
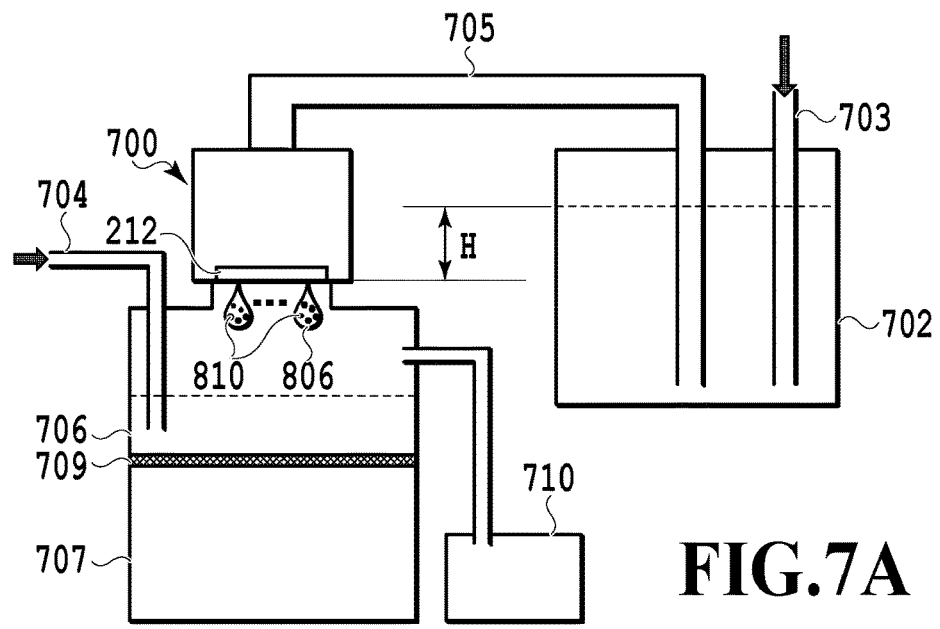
FIG. 7A is a diagram illustrating a UFB-containing liquid manufacturing apparatus in a fourth embodiment of the present invention.
Figure 7B:
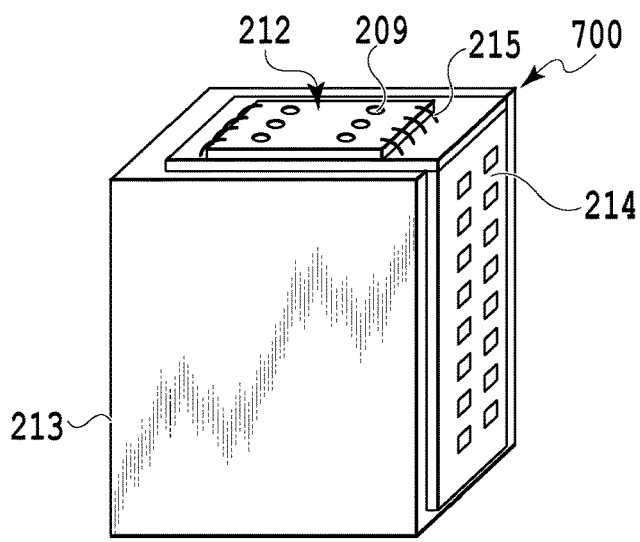
FIG. 7B is a diagram illustrating the UFB-containing liquid manufacturing apparatus in the fourth embodiment of the present invention.

FIG. 7A is a schematic configuration diagram of a UFB generating apparatus in a fourth embodiment of the present invention. The generating apparatus is incorporated into a UFB-containing liquid manufacturing apparatus. FIG. 7B is a schematic perspective diagram of a configuration example of a liquid ejection unit 700 used in the generating apparatus.

The liquid ejection unit 700 of FIG. 7B includes a liquid ejection element 212 that ejects liquid, a liquid tank 213, and a TAB film 214 that is an electrical wiring board provided on one surface of an exterior member of the liquid tank 213. The liquid ejection unit 700 is connected to a control unit of the generating apparatus for controlling the liquid ejection unit 700 via the TAB film 214 for exchanging electrical signals. The TAB film 214 is connected to the liquid ejection element 212 via an electric connection lead 215. The liquid ejection element 212 ejects liquid containing UFBs from ejection openings 209 as will be described later. The liquid ejection unit 700 uses three forms (first, second, and third forms) of mechanism to generate UFBs. In the present embodiment, UFBs are generated by the first form of mechanism.

FIG. 8A to FIG. 8F are cross-sectional views of a liquid ejection portion of the liquid ejection element 212 for illustrating the first form of mechanism to generate UFBs. Between a nozzle member 803 and a substrate 800 that has a heater 801 as a heating resistance element, a pressure chamber (a liquid chamber storing liquid) where the heater 801 is located and a liquid flow channel (supply channel) 802 for supplying liquid into the pressure chamber are formed. In a position on the nozzle member 803 facing the heater 801, the ejection opening 209 communicating with the pressure chamber is formed. Liquid 806 containing a UFB 810 is ejected from the ejection opening 209. The heater 801 is supplied with a pulse signal of constant power via an unshown electrical wiring.

In this embodiment, the heater 801 is powered by an extremely short pulse having a pulse width of about 0.5 μsec to 10.0 μsec.

Figure 8A:
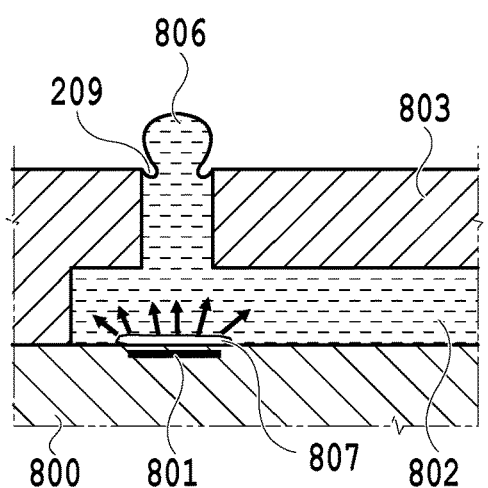
FIG. 8A is a diagram illustrating a UFB generation mechanism in the fourth embodiment of the present invention.

Such short pulses are applied to the heater 801, thereby providing the heater 801 with extremely high heat flux. In a case where a surface temperature of the heater 801 goes close to about 300° C., a phenomenon that appears to be nucleate boiling is observed on the heater 801 at an extremely initial stage (about several picoseconds). After sub-microseconds to several microseconds, a bubble 807 is generated by film boiling as shown in FIG. 8A. At this time, the liquid 806 is slightly extruded from the ejection opening 209.

Figure 8B:
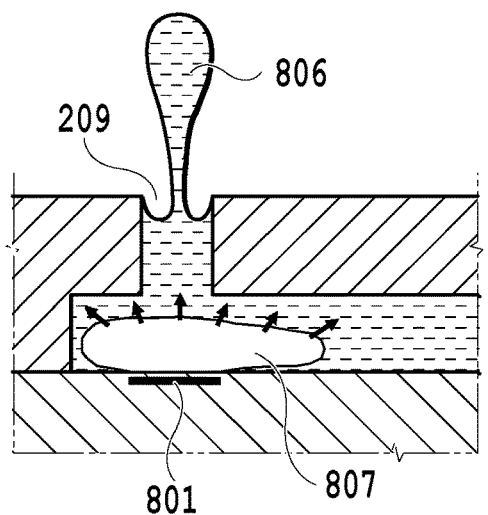
FIG. 8B is a diagram illustrating the UFB generation mechanism in the fourth embodiment of the present invention.
Figure 8C:
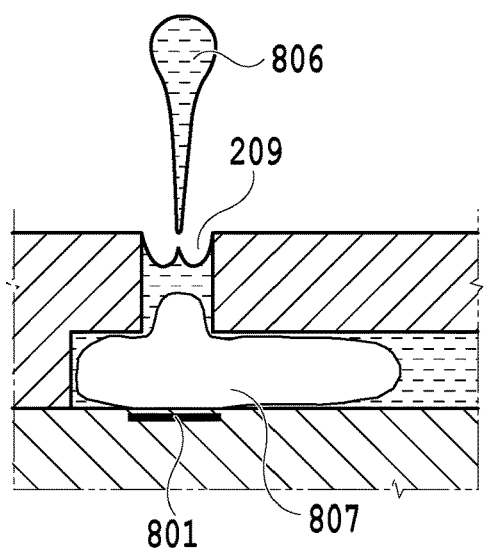
FIG. 8C is a diagram illustrating the UFB generation mechanism in the fourth embodiment of the present invention.

Then, the bubble 807 transitions to its growth stage as shown in FIG. 8B and the liquid 806 is largely extruded from the ejection opening 209. Since the power is continuously supplied to the heater 801 with its surface covered with the bubble 807, the surface temperature of the heater 801 further increases up to about 600 to 800° C. However, the power supply to the heater 801 is stopped at an initial stage of the growth process of the bubble 807. The bubble 807 grows to a maximum bubble with a maximum diameter (about several times the area of the heater) as shown in FIG. 8C and the liquid 806 is separated from the ejection opening 209 and ejected. In this manner, the bubbling energy of the liquid is used to eject the liquid 806 from the ejection opening 209.

Figure 8D:
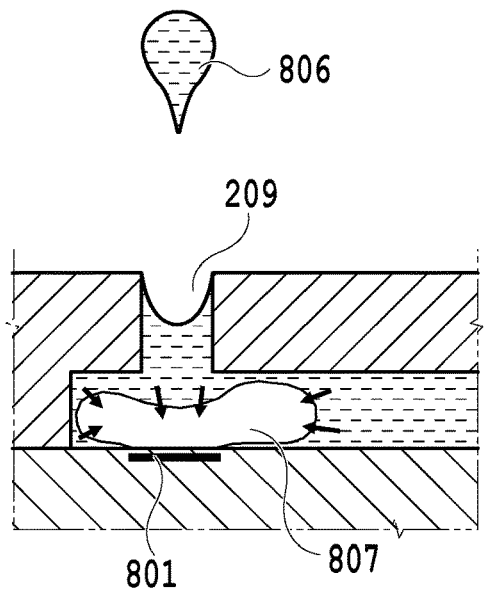
FIG. 8D is a diagram illustrating the UFB generation mechanism in the fourth embodiment of the present invention.
Figure 8E:
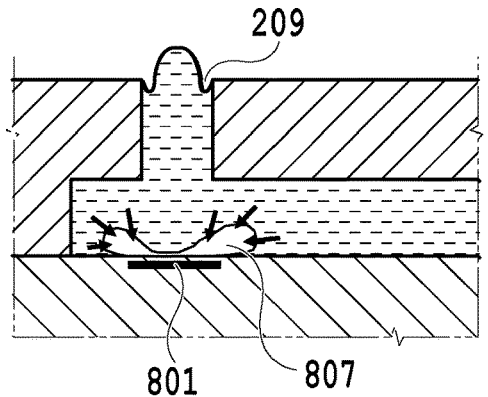
FIG. 8E is a diagram illustrating the UFB generation mechanism in the fourth embodiment of the present invention.
Figure 8F:
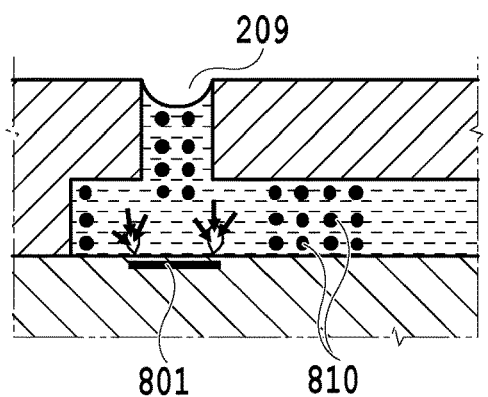
FIG. 8F is a diagram illustrating the UFB generation mechanism in the fourth embodiment of the present invention.

Then, as shown in FIG. 8D, the bubble 807 transitions to its elimination process by negative pressure inside the bubble 807. At this time, the liquid 806 ejected from the ejection opening 209 flies in the air at a speed of about 10 to 20 m/sec. The liquid 806 may be one droplet or may be separated into small droplets or mist droplets. Near the end of the elimination process of the bubble 807, a phenomenon of cavitation I occurs, where liquid touches the surface of the heater 801 again as shown in FIG. 8E. At this time, the surface temperature of the heater 801 decreases to about 100° C. or less (the surface temperature of the heater 801 at this time differs according to a design and film configuration of the heater layer). Then, as shown in FIG. 8F, the bubble is eliminated in at least one extremely small region on the surface of the heater 801, and at this time, spark-like cavitation II occurs.

The mechanical impact forces of the cavitation I and the cavitation II may each have a numerical value roughly equal to or greater than the initial bubbling pressure of film boiling. An impact force per unit area may reach its peak at the occurrence of the cavitation II. Through the stages shown in FIG. 8A to FIG. 8F, the UFBs 810 were generated from gas dissolved in the liquid. As also described with reference to FIG. 3, it is presumed that UFBs are generated through at least the step of FIG. 8A where bubbles are generated by film boiling.

The UFBs 810 thus generated are then contained in the liquid 806 ejected by applying a pulse signal to the heater 801. The liquid 806 containing the UFBs 810 is accumulated in a first collection container 706 shown in FIG. 7A. At this time, it is preferable that the liquid ejection element 212 is in contact with the first collection container 706 (a clearance is allowable to some extent). The liquid 806 may be sucked by a pump 710 depending on the state of the ejected liquid 806 (e.g., the speed, the volume, and the number of small droplets or mist droplets). Further, the liquid 806 may be diluted by adding liquid from a dilution liquid port 704 depending on the number density or bubble diameter of the generated UFBs 810.

The liquid 806 accumulated in the first collection container 706 is moved to a second collection container 707 through a filter 709 to remove impurities other than the UFBs 810 contained therein. A filter diameter of the filter 709 is only required to be equal to or greater than 1.0 μm. The material of the filter 709 is not limited provided that it is insoluble in a liquid to be used. It is preferable that the second collection container 707 is attachable to and detachable from the UFB manufacturing apparatus and capable of being sealed (capped). In view of this, glass is suitable as the material of the second collection container 707. In the case of storing the liquid containing the UFBs 810 in the second collection container 707, the material of the second collection container 707 is required to provide a high degree of protection against gas. Alternatively, the UFBs 810 inside the second collection container 707 may be moved to and stored in another container having a high degree of protection against gas.

As in the second embodiment, 10,000 heaters 801 were provided on one substrate 800 and ten substrates 800 in total were mounted side by side. To the heaters 801, a pulse signal (pulse width: 1.0 μs, voltage: 24V) was applied at a driving frequency of 20 kHz. Pure water was supplied from a liquid supply tank 702 to the liquid ejection unit 700 through a liquid supply pipe 705. At that time, carbonic acid gas was injected from a gas injection port 703 into the pure water inside the liquid supply tank 702 to make the pure water bubble, thereby removing as much air as possible from the pure water and dissolving the carbonic acid gas in the pure water up to near the saturation solubility of carbonic acid gas.

In addition, the liquid 806 can be efficiently ejected from the ejection openings 209 by making a surface of the liquid ejection element 212 equipped with the ejection openings 209 lower than a surface of the liquid inside the liquid supply tank 702 and keeping a difference in hydraulic head H therebetween. That is, in a case where the liquid flow channel 802 or the ejection opening 209 is clogged with foreign matter or bubbles, keeping the difference in hydraulic head H can facilitate carrying the foreign matter or bubbles by hydraulic pressure from the ejection opening 209 into the first collection container 706. As a result, the liquid 806 containing the UFBs 810 can be efficiently manufactured and stored in the first collection container 706 while preventing a situation in which the liquid is not ejected from the ejection opening 209 (liquid ejection failure). It should be noted that, contrary to the case of FIG. 7A, the difference in hydraulic head may be provided by making the surface of the liquid ejection element 212 equipped with the ejection openings 209 higher than the surface of the liquid inside the liquid supply tank 702. In the present embodiment, the liquid ejection element 212 of the liquid ejection unit 700 ejects the liquid 806 downward (in the direction of gravity).

Total Number of Heaters = $1.0e4 \times 10 = 1.0e5 (= 1.0 \times 10^5)$

Number of UFBs Generated =

Figure 7C:
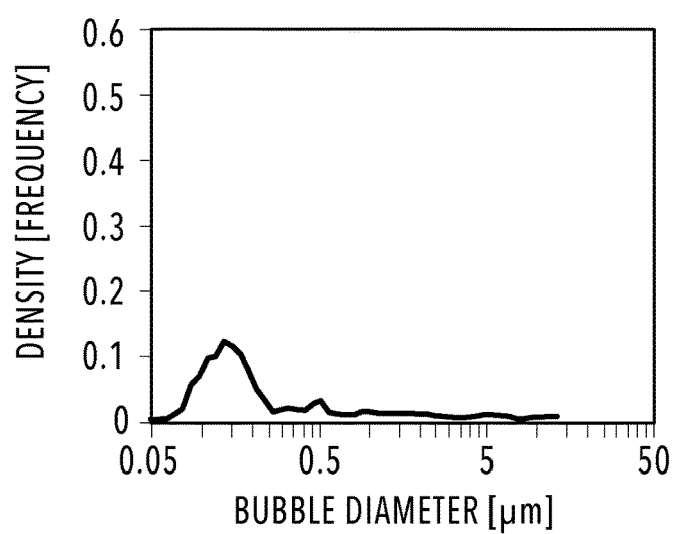
FIG. 7C is a graph illustrating the UFB-containing liquid manufacturing apparatus in the fourth embodiment of the present invention.

$(1.0e5) \times 10 \times (2.0e4) \times 60[s] = 1.2e12 ((UFBs/L)/\min)$ 1.2 billion UFBs 810 per ml were generated in one minute. The UFBs 810 were thus generated in a high number density within an extremely short time. To confirm that, the collected pure water was set in the measurement device SALD-7500 (available from Shimadzu Corp.). As a result of measurement, a number density of UFBs 810 with a diameter of less than 1.0 µm in the pure water was about 1.2 billion per ml. A frequency distribution of bubble diameter at that time is shown in FIG. 7C. The number of UFBs 810 with a diameter ranging from 10 nm to 400 nm was 99.7% of the whole.

Gas contained in the UFBs 810 generated in the above manner was analyzed by the GC-TCD method as in the second embodiment. As a result of the analysis, carbon dioxide ($CO_2$) was detected. The amount of carbon dioxide detected was 10 [mg/L]. Since the saturation solubility of carbonic acid gas in water is about 1.0 [mg/L] at room temperature (about 25° C.), it can be said that the amount of carbonic acid gas contained in the generated UFBs 810 was increased about 10 times. According to the Henry's law stating that "in the case of a gas of low solubility, the amount of gas dissolved in a certain amount of liquid is proportional to the pressure of the gas at a certain temperature", the solubility of gas should not be increased unless the pressure is raised. However, it was shown that gas can be contained in liquid in an amount equal to or higher than its solubility by trapping $CO_2$ inside the UFBs 810 with a diameter of less than 1.0 µm.

Fifth Embodiment

Figure 9A:
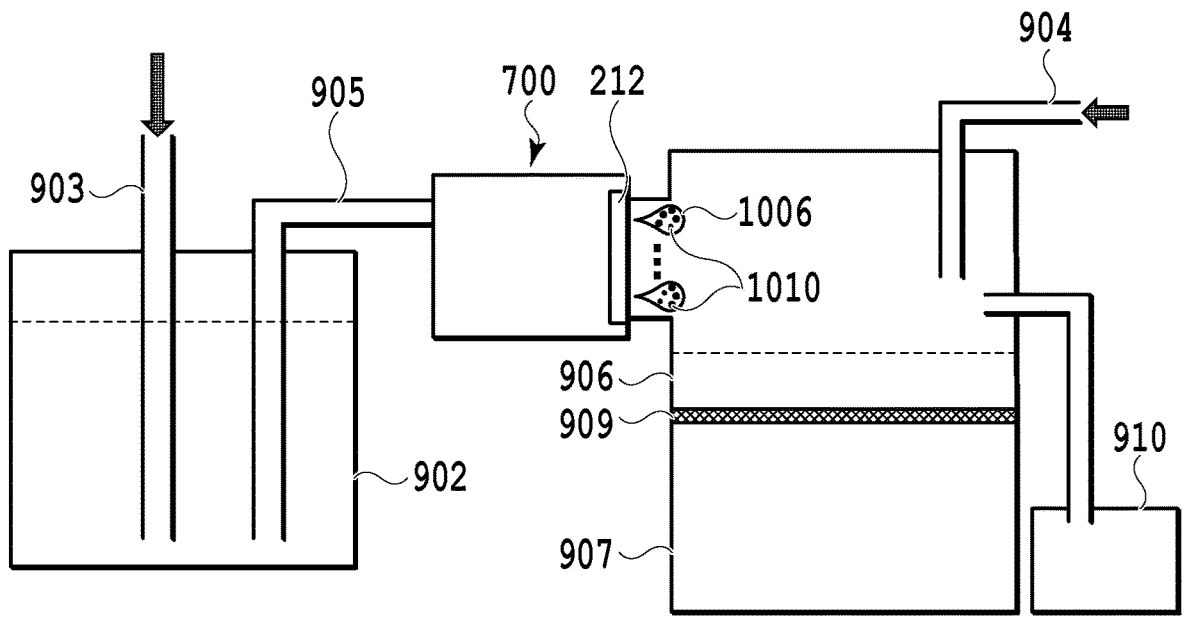
FIG. 9A is a diagram illustrating a UFB-containing liquid manufacturing apparatus in a fifth embodiment of the present invention.

FIG. 9A is a schematic configuration diagram of a bubble generating apparatus in a fifth embodiment of the present invention, which is incorporated into a bubble-containing liquid manufacturing apparatus. As in the fourth embodiment, the liquid ejection unit 700 of FIG. 7B is used in the generating apparatus. A mechanism to generate UFBs in the present embodiment is a second form of mechanism, which is different from the form used in the fourth embodiment. In the second form of mechanism, bubbles generated by film boiling grow to reach their peak, and after this growth process, the bubbles communicate with the outside air in their shrinkage stage.

FIG. 10A to FIG. 10F are cross-sectional views of the liquid ejection portion of the liquid ejection element 212 for illustrating the second form of mechanism to generate UFBs. Between a nozzle member 1003 and a substrate 1000 that has a heater 1001, a pressure chamber where the heater 1001 is located and a liquid flow channel 1002 for supplying liquid into the pressure chamber are formed. In a position on the nozzle member 1003 facing the heater 1001, the ejection opening 209 communicating with the liquid flow channel 1002 is formed. Liquid 1006 containing a UFB 1010 is ejected from the ejection opening 209. The heater 1001 is supplied with a pulse signal of constant power via an unshown electrical wiring. In the present embodiment, the heater 1001 is powered by an extremely short pulse having a pulse width of about 0.5 µsec to 10.0 µsec.

Figure 10A:
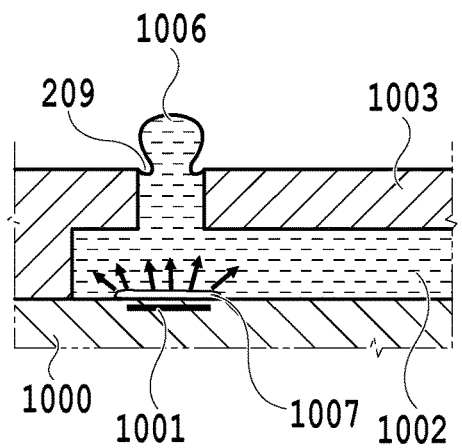
FIG. 10A is a diagram illustrating a UFB generation mechanism in the fifth embodiment of the present invention.

Such short pulses are applied to the heater 1001, thereby providing the heater 1001 with extremely high heat flux. In a case where a surface temperature of the heater 1001 goes close to about 300° C., a phenomenon that appears to be nucleate boiling is observed on the heater 1001 at an extremely initial stage (about several picoseconds). After sub-microseconds to several microseconds, a bubble 1007 is generated by film boiling as shown in FIG. 10A. At this time, the liquid 1006 is slightly extruded from the ejection opening 209.

Figure 10B:
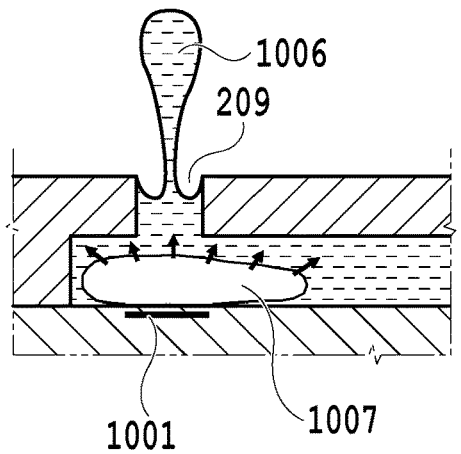
FIG. 10B is a diagram illustrating the UFB generation mechanism in the fifth embodiment of the present invention.
Figure 10C:
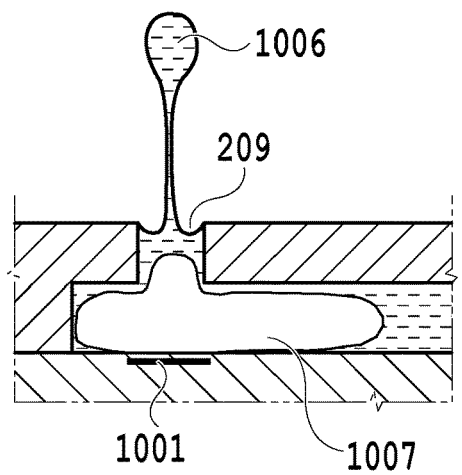
FIG. 10C is a diagram illustrating the UFB generation mechanism in the fifth embodiment of the present invention.

After that, the bubble 1007 transitions to its growth stage as shown in FIG. 10B and the liquid 1006 is largely extruded from the ejection opening 209. Since the power is continuously supplied to the heater 1001 with its surface covered with the bubble 1007, the surface temperature of the heater 1001 further increases up to about 600 to 800° C. However, the power supply to the heater 1001 is stopped at an initial stage of the growth process of the bubble 1007. The bubble 1007 grows to a maximum bubble with a maximum diameter (about several times the area of the heater) as shown in FIG. 10C and the liquid 1006 is stretched from the ejection opening 209 and ejected.

Figure 10D:
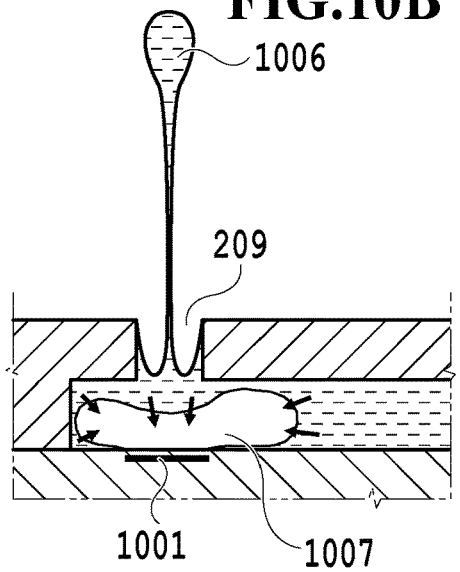
FIG. 10D is a diagram illustrating the UFB generation mechanism in the fifth embodiment of the present invention.
Figure 10E:
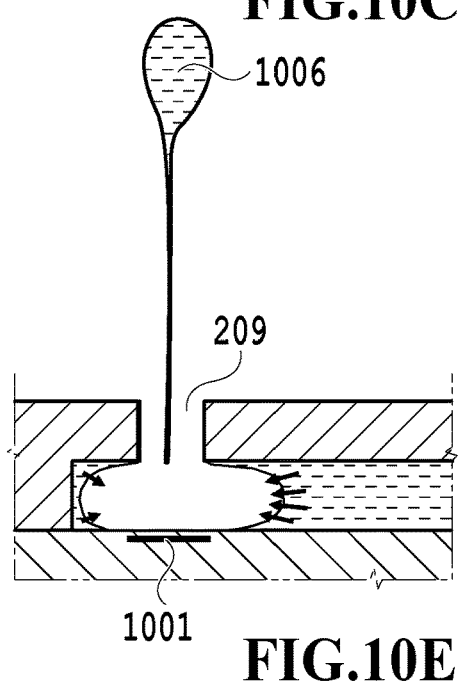
FIG. 10E is a diagram illustrating the UFB generation mechanism in the fifth embodiment of the present invention.
Figure 10F:
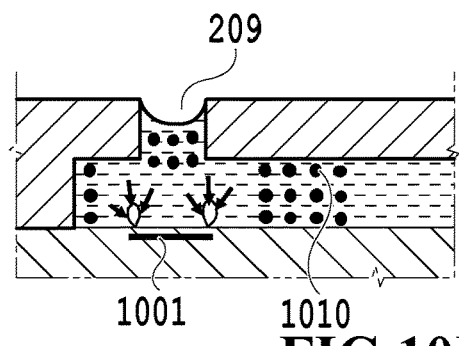
FIG. 10F is a diagram illustrating the UFB generation mechanism in the fifth embodiment of the present invention.

Following that, as shown in FIG. 10D, the bubble 1007 transitions to its elimination process by negative pressure inside the bubble 1007. At this time, the liquid 1006 is further stretched from the ejection opening 209. Near the end of the bubble elimination process, as shown in FIG. 10E, the inside of the bubble 1007 communicates with the air outside the ejection opening 209. Then, as shown FIG. 10F, spark-like cavitation II occurs in at least one extremely small region on the surface of the heater 801.

The mechanical impact force of the cavitation II may have a numerical value roughly equal to or greater than the initial bubbling pressure of film boiling. An impact force per unit area may reach its peak at the occurrence of the cavitation II. Through the stages shown in FIG. 10A to FIG. 10F, the UFBs 1010 were generated from gas dissolved in the liquid. Also in the present embodiment, it is presumed that UFBs are generated through at least the step of FIG. 10A where bubbles are generated by film boiling.

The UFBs 1010 thus generated are then contained in the liquid 1006 ejected by applying a pulse signal to the heater 1001. The liquid 1006 containing the UFBs 1010 is accumulated in a first collection container 906 shown in FIG. 9A. At this time, it is preferable that the liquid ejection element 212 is in contact with the first collection container 906 (a clearance is allowable to some extent). The liquid 1006 may be sucked by a pump 910 depending on the state of the ejected liquid 1006 (e.g., the speed, the volume, and the number of small droplets or mist droplets). Further, the liquid 1006 may be diluted by adding liquid from a dilution liquid port 904 depending on the number density or bubble diameter of the generated UFBs 1010.

The liquid 1006 accumulated in the first collection container 906 is moved to a second collection container 907 through a filter 909 to remove impurities other than the UFBs 1010 contained therein. A filter diameter of the filter 909 is only required to be equal to or greater than 1.0 µm. The material of the filter 909 is not limited provided that it is insoluble in a liquid to be used. It is preferable that the second collection container 907 is attachable to and detachable from the UFB manufacturing apparatus and capable of being sealed (capped). In view of this, glass is suitable as the material of the second collection container 907. In the case of storing the liquid containing the UFBs 1010 in the second collection container 907, the material of the second collection container 907 is required to provide a high degree of protection against gas. Alternatively, the UFBs 1010 inside the second collection container 907 may be moved to and stored in another container having a high degree of protection against gas.

As in the second embodiment, 10,000 heaters 1001 were provided on one substrate 1000. 20 substrates 1000 in total are mounted side by side. To the heaters 1001, a pulse signal (pulse width: 1.0 µs, voltage: 24V) was applied at a driving frequency of 10 kHz. A mixed solution A of liquids listed below was supplied from a liquid supply tank 902 to the liquid ejection unit 700 through a liquid supply pipe 905.

| | |
|---|---|
| Isopropyl Alcohol | 10 wt % |
| Ethylene Glycol | 50 wt % |
| Glycerol | 10 wt % |
| Pure Water | 30 wt % |

At that time, oxygen gas was injected from a gas injection port 903 into the mixed solution A inside the liquid supply tank 902 to make the mixed solution A bubble, thereby removing as much air as possible from the mixed solution A and dissolving the oxygen gas in the mixed solution A up to near the saturation solubility of oxygen gas. In the present embodiment, the liquid ejection element 212 of the liquid ejection unit 700 ejects the liquid 1006 laterally (horizontally).

$$\text{Total Number of Heaters} = 1.0e4 \times 20 = 2.0e5 (= 2.0 \times 10^5)$$

Number of UFBs Generated =

$$(2.0e5) \times 10 \times (1.0e4) \times 60[s] = 1.2e12 ((UFBs/L)/\min)$$

Figure 9B:
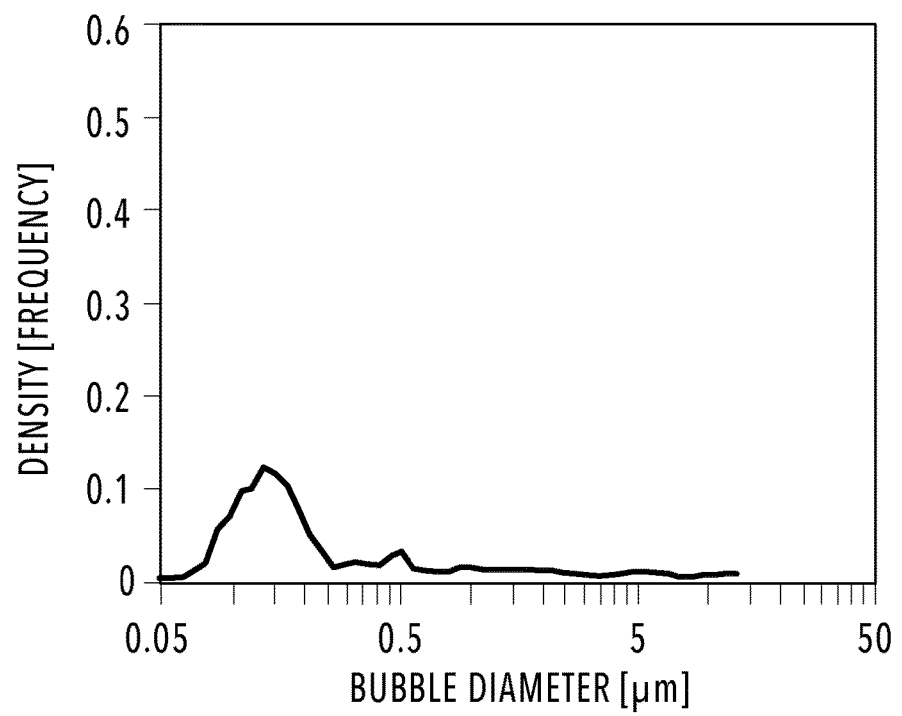
FIG. 9B is a graph illustrating the UFB-containing liquid manufacturing apparatus in the fifth embodiment of the present invention.

1.2 billion UFBs 1010 per ml were generated in one minute. The UFBs 1010 were thus generated in a high number density within an extremely short time. To confirm that, the collected mixed solution A was set in the measurement device SALD-7500 (available from Shimadzu Corp.). As a result of measurement, a number density of UFBs 1010 with a diameter of less than 1.0 µm in the mixed solution was about 1.2 billion per ml. A frequency distribution of bubble diameter at that time is shown in FIG. 9B. The number of UFBs 1010 with a diameter ranging from 10 nm to 400 nm was 99.7% of the whole. In addition, gas contained in the UFBs 1010 generated in the above manner was analyzed by the GC-TCD method as in the second embodiment. As a result of the analysis, oxygen was detected. The amount of oxygen detected was 8 [mg/L].

Sixth Embodiment

Figure 11A:
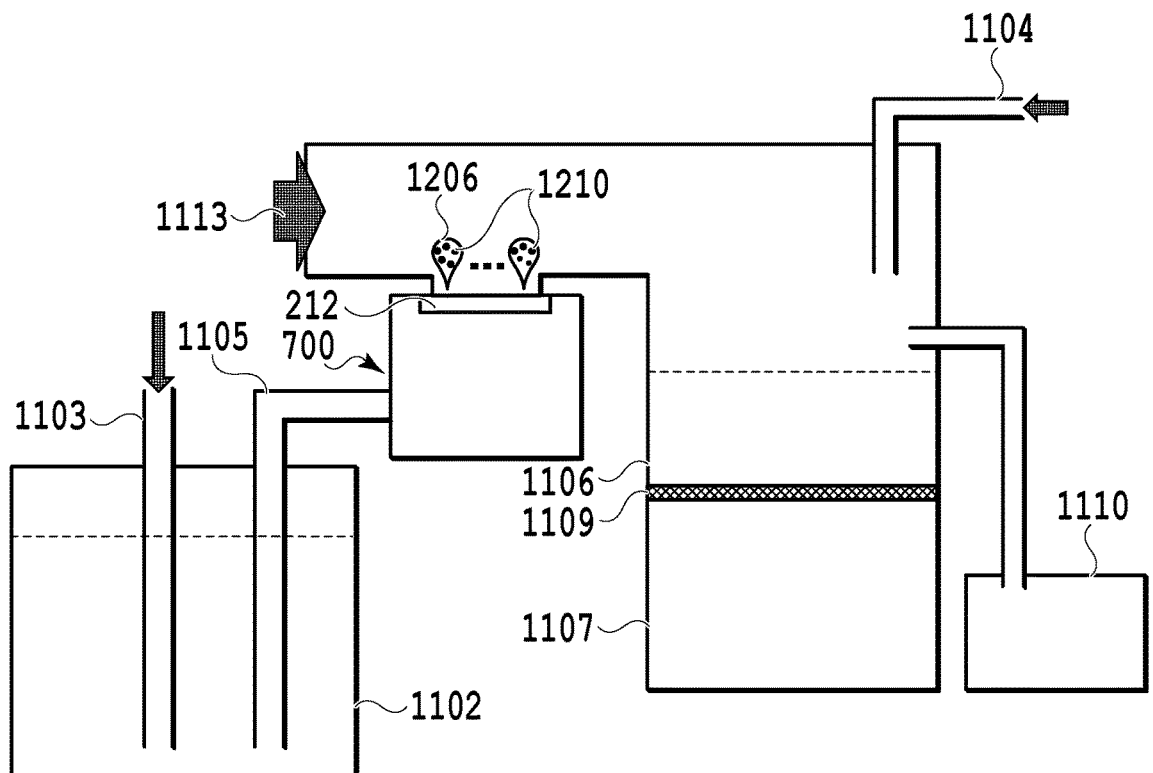
FIG. 11A is a diagram illustrating a UFB-containing liquid manufacturing apparatus in a sixth embodiment of the present invention.

FIG. 11A is a schematic configuration diagram of a UFB generating apparatus in a sixth embodiment of the present invention, which is incorporated into a UFB-containing liquid manufacturing apparatus. As in the fourth embodiment, the liquid ejection unit 700 of FIG. 7B is used in the generating apparatus. A mechanism to generate UFBs in the present embodiment is a third form of mechanism, which is different from either of the forms used in the fourth and fifth embodiments. In the third form of mechanism, bubbles generated by film boiling communicate with the outside air in their growth stage.

FIG. 12A to FIG. 12E are cross-sectional views of the liquid ejection portion of the liquid ejection element 212 for illustrating the third form of mechanism to generate UFBs. Between a nozzle member 1203 and a substrate 1200 that has a heater 1201, a pressure chamber where the heater 1201 is located and a liquid flow channel 1202 for supplying liquid into the pressure chamber are formed. In a position on the nozzle member 1203 facing the heater 1201, the ejection opening 209 communicating with a liquid flow channel 1202 is formed. Liquid 1206 containing a UFB 1210 is ejected from the ejection opening 209. The heater 1201 is supplied with a pulse signal of constant power via an unshown electrical wiring. In the present embodiment, the heater 1201 is powered by an extremely short pulse having a pulse width of about 0.5 µsec to 10.0 µsec.

Figure 12A:
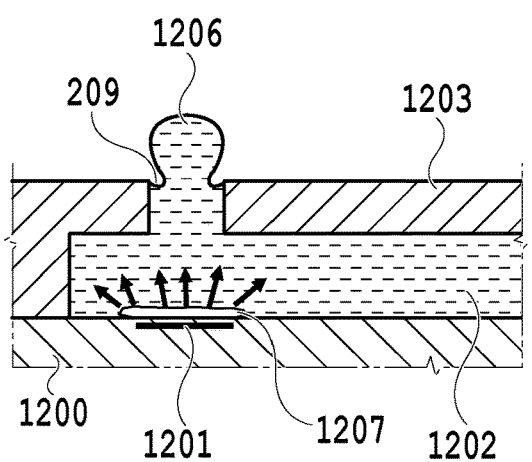
FIG. 12A is a diagram illustrating a UFB generation mechanism in the sixth embodiment of the present invention.

Such short pulses are applied to the heater 1201, thereby providing the heater 1201 with extremely high heat flux. In a case where a surface temperature of the heater 1201 goes close to about 300° C., a phenomenon that appears to be nucleate boiling is observed on the heater 1201 at an extremely initial stage (about several picoseconds). After sub-microseconds to several microseconds, a bubble 1207 is generated by film boiling as shown in FIG. 12A. At this time, the liquid 1206 is slightly extruded from the ejection opening 209.

Figure 12B:
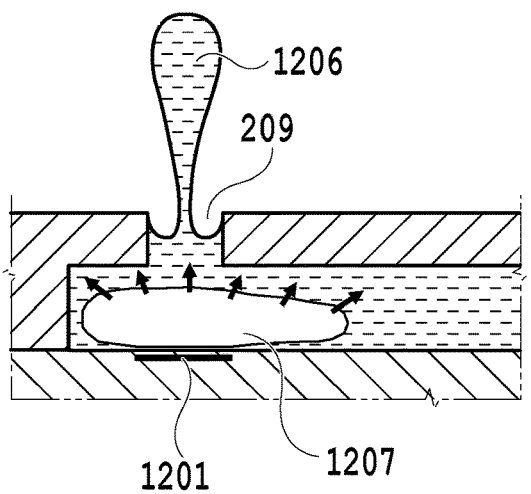
FIG. 12B is a diagram illustrating the UFB generation mechanism in the sixth embodiment of the present invention.
Figure 12C:
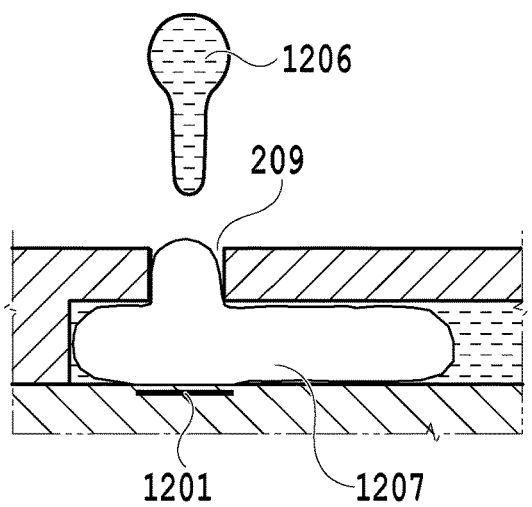
FIG. 12C is a diagram illustrating the UFB generation mechanism in the sixth embodiment of the present invention.
Figure 12D:
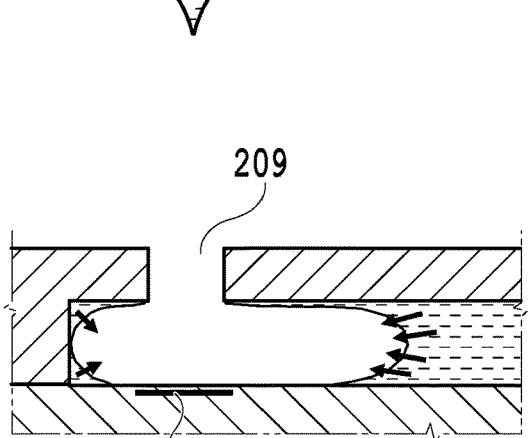
FIG. 12D is a diagram illustrating the UFB generation mechanism in the sixth embodiment of the present invention.
Figure 12E:
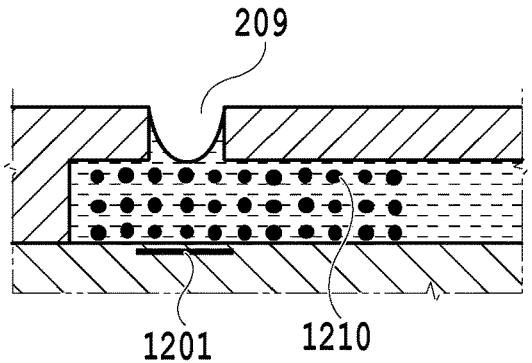
FIG. 12E is a diagram illustrating the UFB generation mechanism in the sixth embodiment of the present invention.

After that, the bubble 1207 transitions to its growth stage as shown in FIG. 12B and the liquid 1206 is largely extruded from the ejection opening 209. Since the power is continuously supplied to the heater 1201 with its surface covered with the bubble 1207, the surface temperature of the heater 1201 further increases up to about 600 to 800° C. However, the power supply to the heater 1201 is stopped at an initial stage of the growth process of the bubble 1207. The bubble 1207 grows as shown in FIG. 12C. At this time, the bubble 1207 is slightly extruded from the ejection opening 209 and the liquid 1206 is stretched a little from the ejection opening 209 and ejected. After that, as shown in FIG. 12D, the bubble 1207 communicates with the outside air through the ejection opening 209. Then, as shown in FIG. 12E, liquid is refilled from an unshown liquid tank through the liquid flow channel 1202. Through the stages shown in FIG. 12A to FIG. 12E, the UFBs 1210 were generated from gas dissolved in the liquid. Also in the present embodiment, it is presumed that UFBs are generated through at least the step of FIG. 12A where bubbles are generated by film boiling.

The UFBs 1210 thus generated are then contained in the liquid 1206 ejected by applying a pulse signal to the heater 1201. The liquid 1206 containing the UFBs 1210 is accumulated in a first collection container 1106 shown in FIG. 11A. At this time, it is preferable that the liquid ejection element 212 is in contact with the first collection container 1106 (a clearance is allowable to some extent). In the present embodiment, the liquid ejection element 212 of the liquid ejection unit 700 ejects the liquid 1206 upward (in the direction opposite to the direction of gravity). Accordingly, fresh air (it is preferable that the air is purity-controlled factory air or the like) is blown from an air blowing port 1113 to improve the efficiency in collection of the liquid 1206 in the first collection container 1106. The liquid 1206 may be sucked by a pump 1110 depending on the state of the ejected liquid 1206 (e.g., the speed, the volume, and the number of small droplets or mist droplets). Further, the liquid 1206 may be diluted by adding liquid from a dilution liquid port 1104 depending on the number density or bubble diameter of the generated UFBs 1210.

The liquid 1206 accumulated in the first collection container 1106 is moved to a second collection container 1107 through a filter 1109 to remove impurities other than the UFBs 1210 contained therein. A filter diameter of the filter 1109 is only required to be equal to or greater than 1.0 µm. The material of the filter 1109 is not limited provided that it is insoluble in a liquid to be used. It is preferable that the second collection container 1107 is attachable to and detachable from the UFB manufacturing apparatus and capable of being sealed (capped). In view of this, glass is suitable as the material of the second collection container 1107. In the case of storing the liquid containing the UFBs 1210 in the second collection container 1107, the material of the second collection container 1107 is required to provide a high degree of protection against gas. Alternatively, the UFBs 1210 inside the second collection container 1107 may be moved to and stored in another container having a high degree of protection against gas.

As in the second embodiment, 10,000 heaters 1201 were provided on one substrate 1200. 40 substrates 1200 in total were mounted side by side. To the heaters 1201, a pulse signal (pulse width: 1.0 µs, voltage: 24V) was applied at a driving frequency of 5 kHz. A mixed solution B of liquids listed below was supplied from a liquid supply tank 1102 to the liquid ejection unit 700 through a liquid supply pipe 1105.

| Isopropyl Alcohol | 5 wt % |
|---|---|
| Ethylene Glycol | 30 wt % |
| Glycerol | 5 wt % |
| Pure Water | 60 wt % |

At that time, hydrogen gas was injected from a gas injection port 1103 into the mixed solution B inside the liquid supply tank 1102 to make the mixed solution B bubble, thereby removing as much air as possible from the mixed solution B and dissolving the hydrogen gas in the mixed solution B up to near the saturation solubility of hydrogen gas.

Total Number of Heaters = $1.0e4 \times 40 = 4.0e5 (= 4.0 \times 10^5)$

Number of UFBs Generated =

Figure 11B:
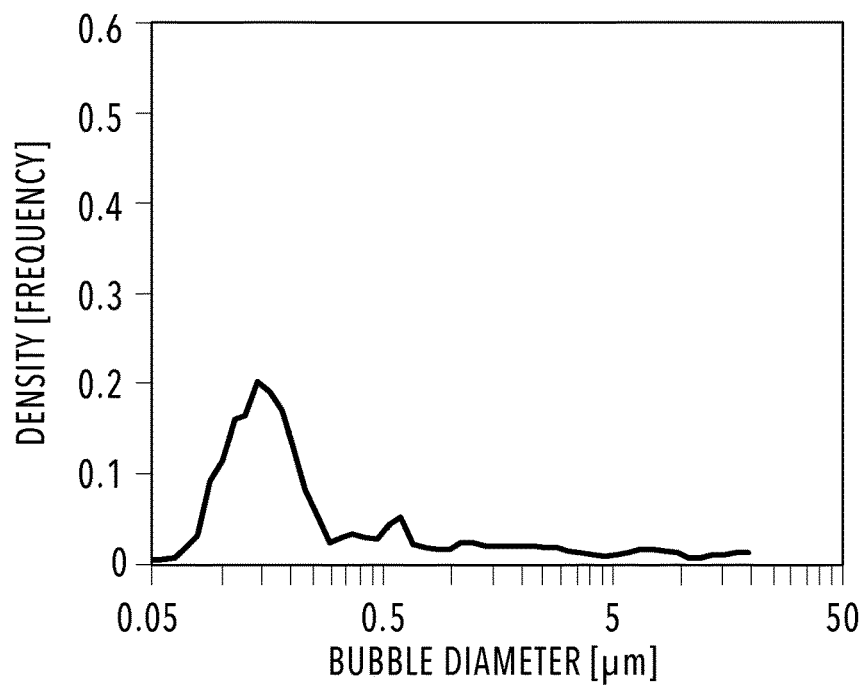
FIG. 11B is a graph illustrating the UFB-containing liquid manufacturing apparatus in the sixth embodiment of the present invention.

$(4.0e5) \times 10 \times (5.0e3) \times 60[s] = 1.2e12 ((UFBs/L)/\min)$ 1.2 billion UFBs 1210 per ml were generated in one minute. The UFBs 1210 were thus generated in a high number density within an extremely short time. To confirm that, the collected mixed solution B was set in the measurement device SALD-7500 (available from Shimadzu Corp.). As a result of measurement, a number density of UFBs 1010 with a diameter of less than 1.0 µm in the mixed solution B was about 1.2 billion per ml. A frequency distribution of bubble diameter at that time is shown in FIG. 11B. The number of UFBs 1210 with a diameter ranging from 10 nm to 400 nm was 99.7% of the whole. In addition, gas contained in the UFBs 1210 generated in the above manner was analyzed by the GC-TCD method as in the second embodiment. As a result of the analysis, hydrogen was detected. The amount of hydrogen detected was 4 [mg/L].

According to the fourth to sixth embodiments of the present invention, UFBs can also be efficiently generated by heating liquid by means of the heater, causing film boiling in the liquid, generating bubbles, and using the pressure of the bubbles to cause liquid droplets containing UFBs to fly.

Seventh Embodiment

Figure 13A:
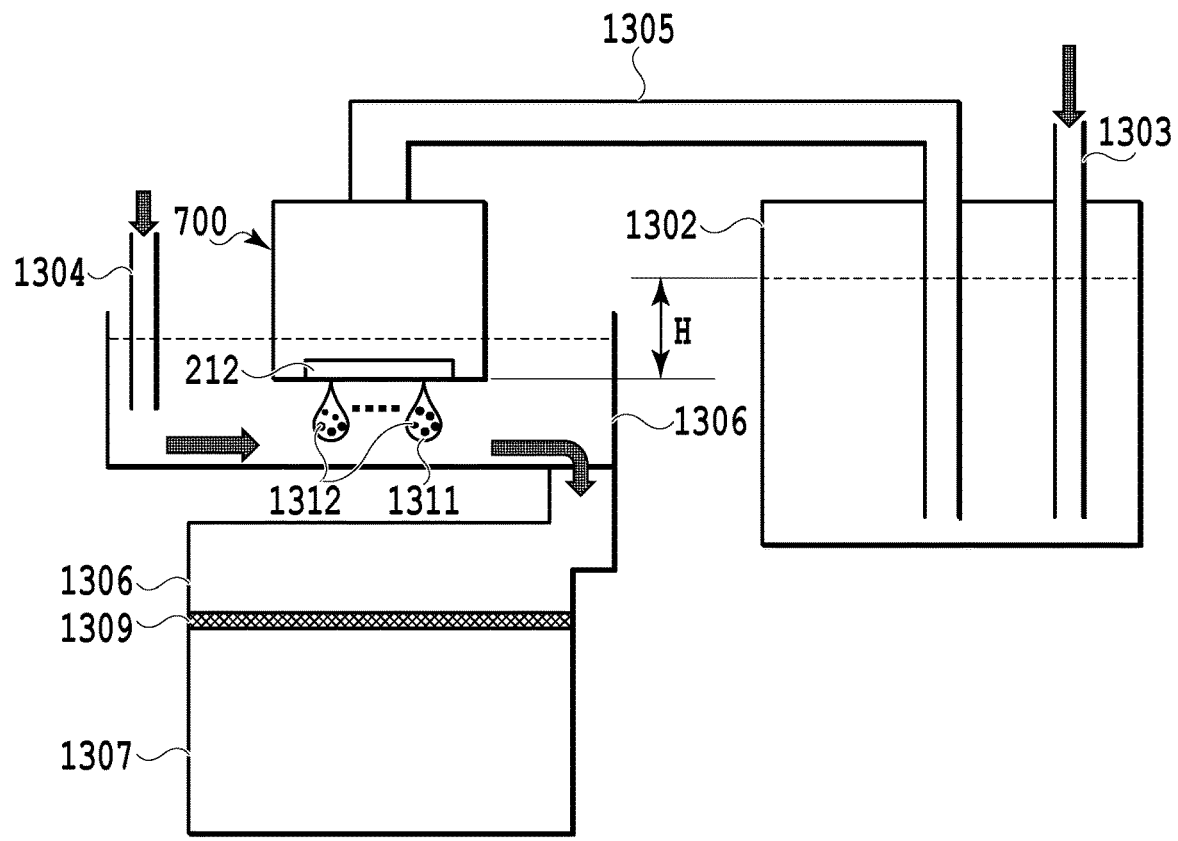
FIG. 13A is a diagram illustrating a UFB-containing liquid manufacturing apparatus in a seventh embodiment of the present invention.

FIG. 13A is a schematic configuration diagram of a bubble generating apparatus in a seventh embodiment of the present invention, which is incorporated into a bubble-containing liquid manufacturing apparatus. As in the fourth embodiment, the liquid ejection unit 700 of FIG. 7B is used in the generating apparatus. A mechanism to generate UFBs in the present embodiment is the first form of mechanism which is also used in the fourth embodiment. In the present embodiment, bubbles are generated by causing film boiling with ejection openings soaked into pure water and liquid 1311 containing UFBs is ejected into the pure water.

As in the fourth embodiment, 10,000 heaters 801 were provided on one substrate 800. 20 substrates 800 in total were mounted side by side. To the heaters 801, a pulse signal (pulse width: 1.0 µs, voltage: 24V) was applied at a driving frequency of 20 kHz. Pure water was supplied from a liquid supply tank 1302 to the liquid ejection unit 700 through a liquid supply pipe 1305. At that time, ozone gas was injected from a gas injection port 1303 into the pure water inside the liquid supply tank 1302 to make the pure water bubble, thereby removing as much air as possible from the pure water and dissolving the ozone gas in the pure water up to near the saturation solubility of ozone gas.

In addition, the liquid 1311 can be efficiently ejected from the ejection openings 209 by making a surface of the liquid ejection element 212 equipped with the ejection openings 209 lower than a surface of the liquid inside the liquid supply tank 1302 and keeping a difference in hydraulic head H therebetween. That is, in a case where the liquid flow channel or the ejection opening 209 in the liquid ejection portion of the liquid ejection element 212 is clogged with foreign matter or bubbles, keeping the difference in hydraulic head H can facilitate carrying the foreign matter or bubbles by hydraulic pressure from the ejection opening 209 into the first collection container 1306. As a result, the liquid 1311 containing the UFBs 1312 can be efficiently manufactured and stored in the first collection container 1306 while preventing a situation in which the liquid is not ejected from the ejection opening 209 (liquid ejection failure). Pure water is supplied from a liquid supply port 1304 so that a surface of the pure water inside the first collection container 1306 is higher than the position of the ejection openings 209 of the liquid ejection element 212. This allows the ejection openings 209 to be soaked into the pure water. A flow of pure water is formed inside the first collection container 1306. The pure water containing numerous UFBs 1312 is stored in a second collection container 1307 through a filter 1309. The liquid ejection element 212 in the liquid ejection unit 700 ejects the liquid 1311 downward (in the direction of gravity).

Total Number of Heaters = $1.0e4 \times 20 = 2.0e5 (= 2.0 \times 10^5)$

Number of UFBs Generated =

Figure 13B:
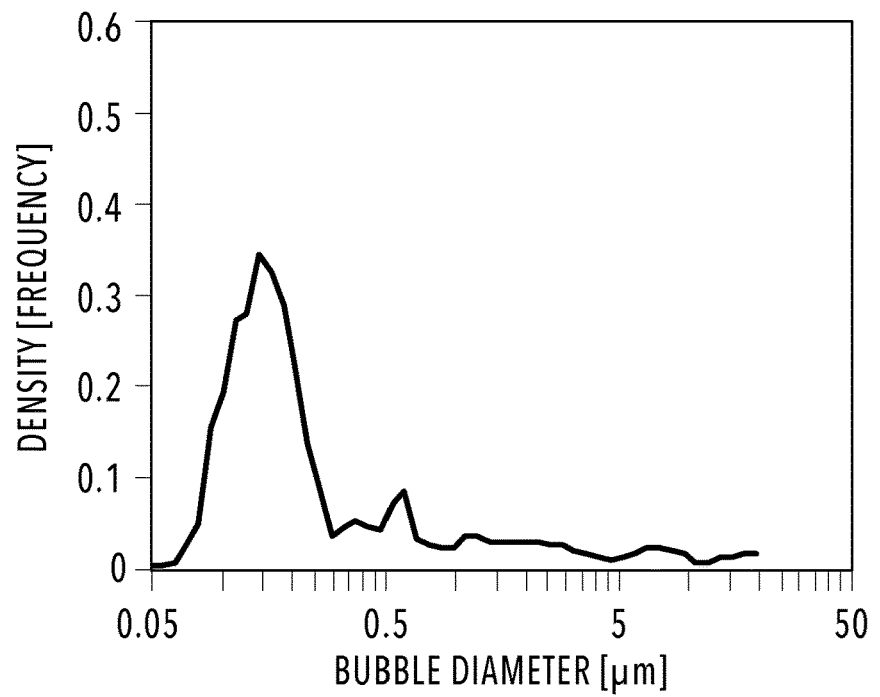
FIG. 13B is a graph illustrating the UFB-containing liquid manufacturing apparatus in the seventh embodiment of the present invention.

$(2.0e5) \times 10 \times (2.0e4) \times 60[s] = 2.4e12 ((UFBs/L)/\min)$ 2.4 billion UFBs 1312 per ml were generated in one minute. The UFBs 1312 were thus generated in a high number density within an extremely short time. To confirm that, the collected pure water was set in the measurement device SALD-7500 (available from Shimadzu Corp.). As a result of measurement, a number density of UFBs 1312 with a diameter of less than 1.0 µm in the pure water was about 2.4 billion per ml. A frequency distribution of bubble diameter at that time is shown in FIG. 13B. The number of UFBs 1312 with a diameter ranging from 10 nm to 400 nm was 99.7% of the whole.

Gas contained in the UFBs 1312 generated in the above manner was analyzed by the GC-TCD method as in the second embodiment. As a result of the analysis, ozone ($O_3$) was detected. The amount of ozone detected was 20 [mg/L]. Since ozone is an unstable gas and has the property of oxidation-reduction, it normally decomposes itself into oxygen and water. However, the amount of ozone contained in the UFBs 1312 generated in the present embodiment was not changed even after two months.

Eighth Embodiment

Figure 14A:
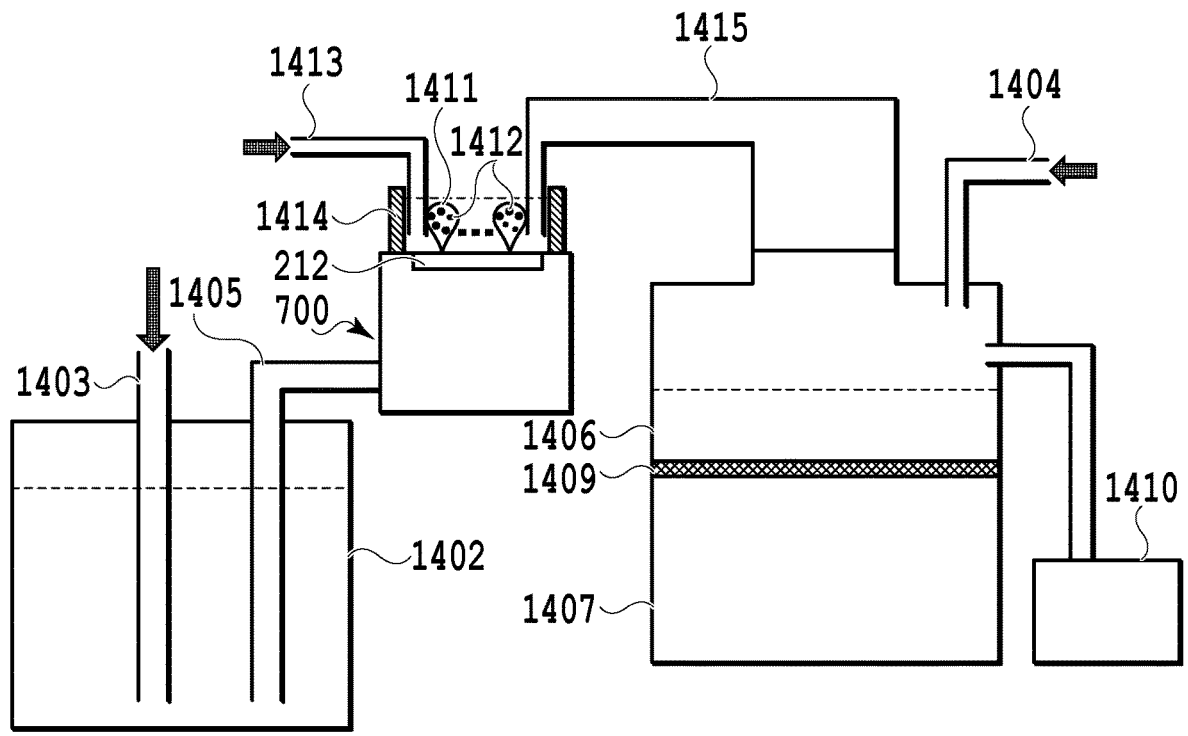
FIG. 14A is a diagram illustrating a UFB-containing liquid manufacturing apparatus in an eighth embodiment of the present invention.

FIG. 14A is a schematic configuration diagram of a bubble generating apparatus in an eighth embodiment of the present invention, which is incorporated into a bubble-containing liquid manufacturing apparatus. As in the fourth embodiment, the liquid ejection unit 700 of FIG. 7B is used in the generating apparatus. A mechanism to generate UFBs in the present embodiment is the first form of mechanism which is also used in the fourth embodiment. In the present embodiment, bubbles are generated by causing film boiling with ejection openings soaked into pure water, and liquid 1311 containing UFBs is ejected into the pure water like the seventh embodiment. However, the direction of ejection is different from that in the seventh embodiment.

As in the fourth embodiment, 10,000 heaters 801 were provided on one substrate 800. 30 substrates 800 in total were mounted side by side. To the heaters 801, a pulse signal (pulse width: 1.0 μs, voltage: 24V) was applied at a driving frequency of 20 kHz. Pure water was supplied from a liquid supply tank 1402 to the liquid ejection unit 700 through a liquid supply pipe 1405. At that time, fluorine gas was injected from a gas injection port 1403 into the pure water inside the liquid supply tank 1402 to make the pure water bubble, thereby removing as much air as possible from the pure water and dissolving the fluorine gas in the pure water up to near the saturation solubility of fluorine gas.

The liquid ejection element 212 of the liquid ejection unit 700 forces liquid 1411 out upward (in the direction opposite to the direction of gravity). The liquid ejection unit 700 has a bank 1414 that entirely surrounds the ejection openings 209 of the liquid ejection element 212. The pure water is supplied to the inside of the bank 1414 from a liquid supply port 1413. A region surrounded with the bank 1414 is filled with the pure water, in which the liquid ejection element 212 is soaked. The liquid 1411 containing UFBs 1412 is forced out of the liquid ejection element 212. The pure water containing numerous UFBs 1412 is accumulated in the region surrounded with the bank 1414 and then moved by the suction of a pump 1410 to a first collection container 1406 through a pipe 1415. The pure water, which contains the UFBs 1412 and is stored in the first collection container 1406, is then accumulated in a second collection container 1407 through a filter 1409.

$$\text{Total Number of Heaters} = 1.0e4 \times 30 = 3.0e5 (= 30 \times 10^5)$$

Number of UFBs Generated =

$$(3.0e5) \times 10 \times (2.0e4) \times 60[s] = 3.6e12 ((UFBs/L)/\min)$$

Figure 14B:
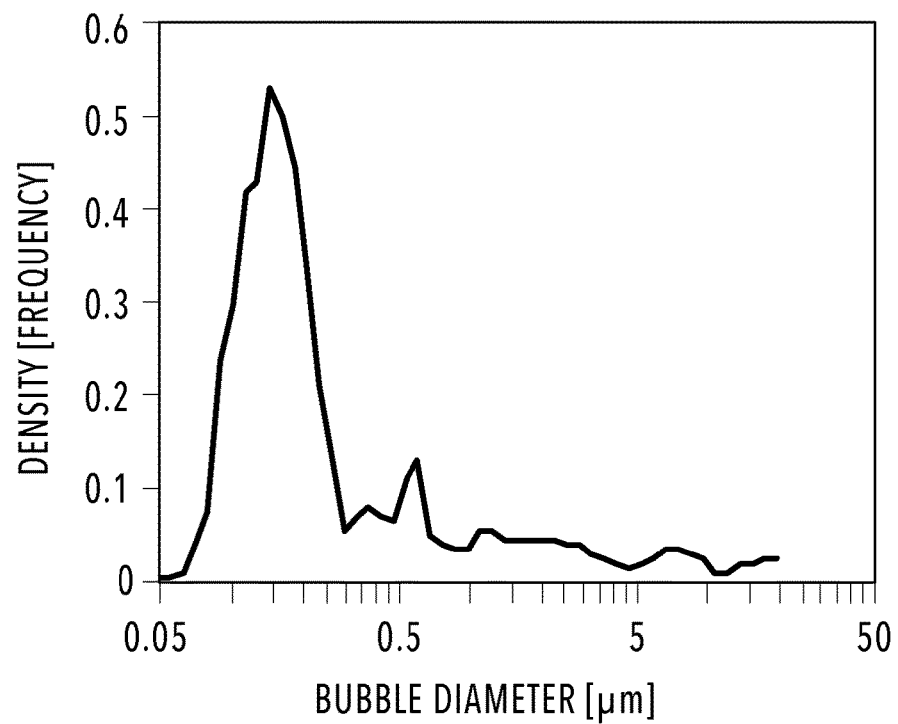
FIG. 14B is a graph illustrating the UFB-containing liquid manufacturing apparatus in the eighth embodiment of the present invention.

3.6 billion UFBs 1412 per ml were generated in one minute. The UFBs 1412 were thus generated in a high number density within an extremely short time. To confirm that, the collected pure water was set in the measurement device SALD-7500 (available from Shimadzu Corp.). As a result of measurement, a number density of UFBs 1412 with a diameter of less than 1.0 μm in the pure water was about 3.6 billion per ml. A frequency distribution of bubble diameter at that time is shown in FIG. 14B. The number of UFBs 1412 with a diameter ranging from 10 nm to 400 nm was 99.7% of the whole. Gas contained in the UFBs 1412 generated in the above manner was analyzed by the GC-TCD method as in the second embodiment. As a result of the analysis, fluorine ($F_2$) was detected. The amount of fluorine detected was 10 [mg/L].

Ninth Embodiment

Figure 15A:
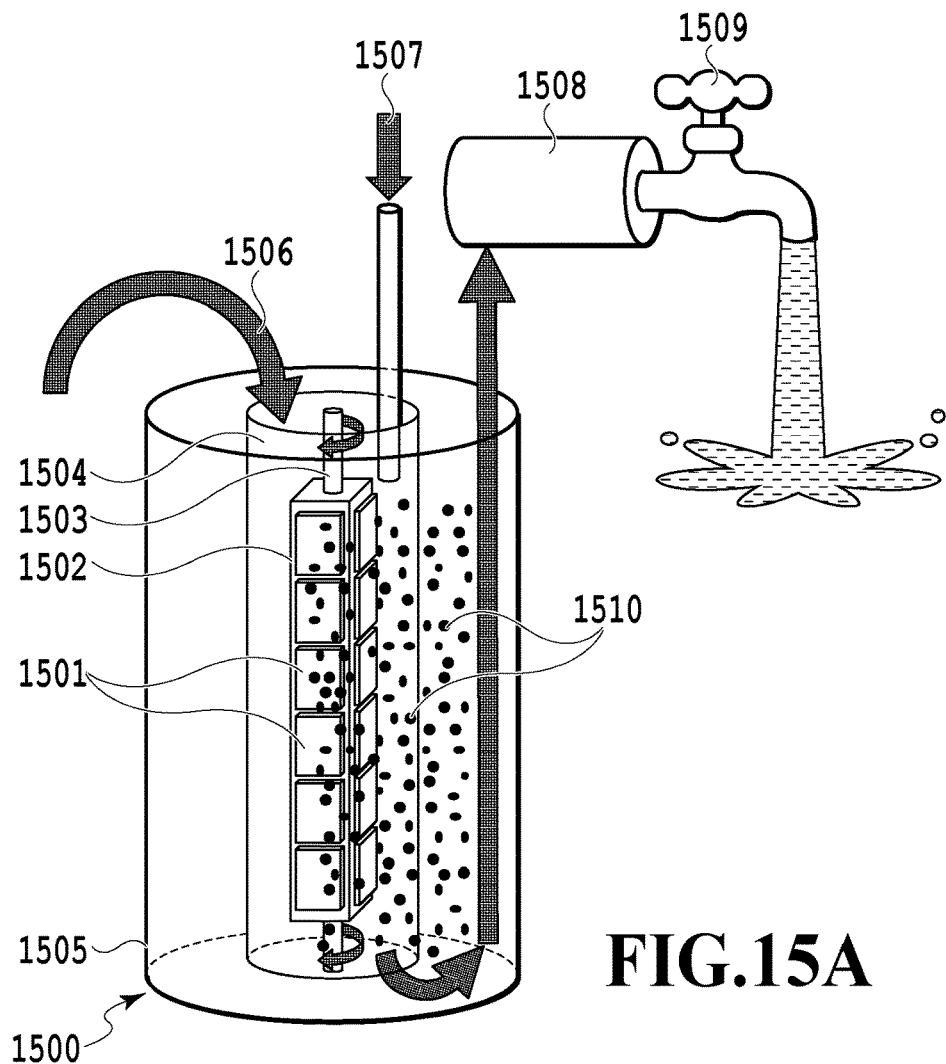
FIG. 15A is a diagram illustrating a UFB-containing liquid manufacturing apparatus in a ninth embodiment of the present invention.

FIG. 15A is a schematic configuration diagram of a bubble generating apparatus according to a ninth embodiment of the present invention, which is incorporated into a water purifier 1500 serving as a bubble-containing liquid manufacturing apparatus. The four side surfaces of a holding member 1502 having the shape of a rectangular parallelepiped are equipped with a plurality of substrates 1501 each having heaters 2 like the substrate 1 shown in FIG. 1. The holding member 1502 is rotated about a rotating shaft 1503 extending vertically. The holding member 1502 and the rotating shaft 1503 are located inside a first water storage container 1504, which is a liquid chamber. The water storage container 1504 is supplied with tap water from a supply port 1506. A second water storage container 1505 is provided outside the first water storage container 1504.

Like the first embodiment, liquid is heated by the heaters 2, film boiling is caused, and bubbles are generated in the liquid, whereby UFBs 1510 are generated. Much of the UFBs 1510 is contained in the tap water inside the first water storage container 1504. The tap water containing the UFBs 1510 flows downward along a flow of tap water inside the first water storage container 1504 while being stirred by the rotation of the holding member 1502. Then, the tap water flows in between the first water storage container 1504 and the second water storage container 1505 from the lower end of the first water storage container 1504, and is discharged from a tap 1509 through a pipe 1508. Nitrogen gas is blown from a gas blowing port 1507 into the tap water inside the first water storage container 1504. Since large bubbles of the nitrogen gas float up against the flow of tap water inside the first water storage container 1504 due to buoyancy exerted on them, they are prevented from flowing in between the first water storage container 1504 and the second water storage container 1505.

10,000 heaters were provided on one substrate 1501, and 25 substrates 1501 were mounted on each of the four side surfaces of the holding member 1502, with the result that 100 substrates 1501 were mounted in total. To the heaters, a pulse signal (pulse width: 5.0 μs, voltage: 18 V) was applied at a driving frequency of 20 kHz. A flow velocity of tap water supplied from the supply port 1506 was set at 1.0 L/min. Nitrogen gas was continuously blown from the gas blowing port 1507 into the tap water inside the first water storage container 1504.

$$\text{Total Number of Heaters} = 1.0e4 \times 100 = 1.0e6 (= 1.0 \times 10^6)$$

Number of UFBs Generated =

$$(1.0e6) \times 1.0 \times (2.0e4) \times 60[s] = 1.2e12 ((UFBs/L)/\min)$$

Figure 15B:
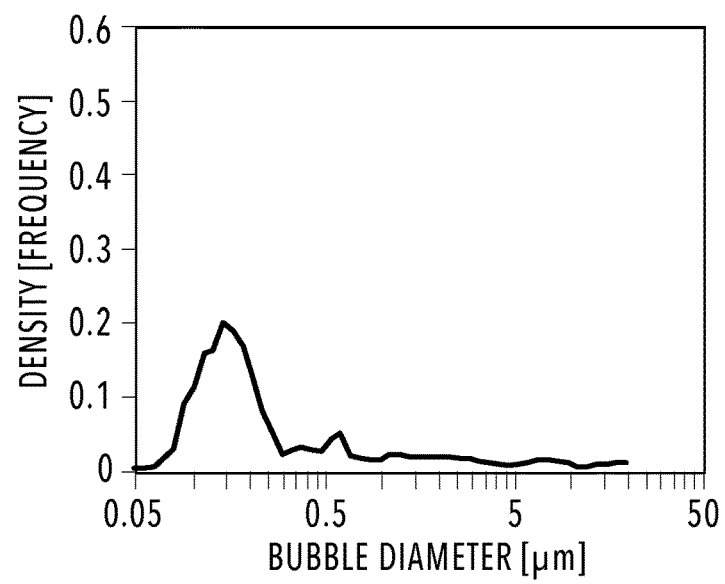
FIG. 15B is a graph illustrating the UFB-containing liquid manufacturing apparatus in the ninth embodiment of the present invention.

1.2 billion UFBs 1510 per ml were generated in one minute. The UFBs 1510 were thus generated in a high number density within an extremely short time. To confirm that, the collected tap water was set in the measurement device SALD-7500 (available from Shimadzu Corp.). As a result of measurement, a number density of UFBs 1510 with a diameter of less than 1.0 μm in the tap water was about 1.2 billion per ml. A frequency distribution of bubble diameter at that time is shown in FIG. 15B. The number of UFBs 1510 with a diameter ranging from 10 nm to 400 nm was 99.8% of the whole. Further, the number of UFBs 1510 generated in one series of steps from the stages (a) through (f) in FIG. 3 was about one. Gas contained in the UFBs 1510 generated in the above manner was analyzed by the GC-TCD method as in the second embodiment. As a result of the analysis, nitrogen was detected. The amount of nitrogen detected was 16 [mg/L].

Tenth Embodiment

Figure 16A:
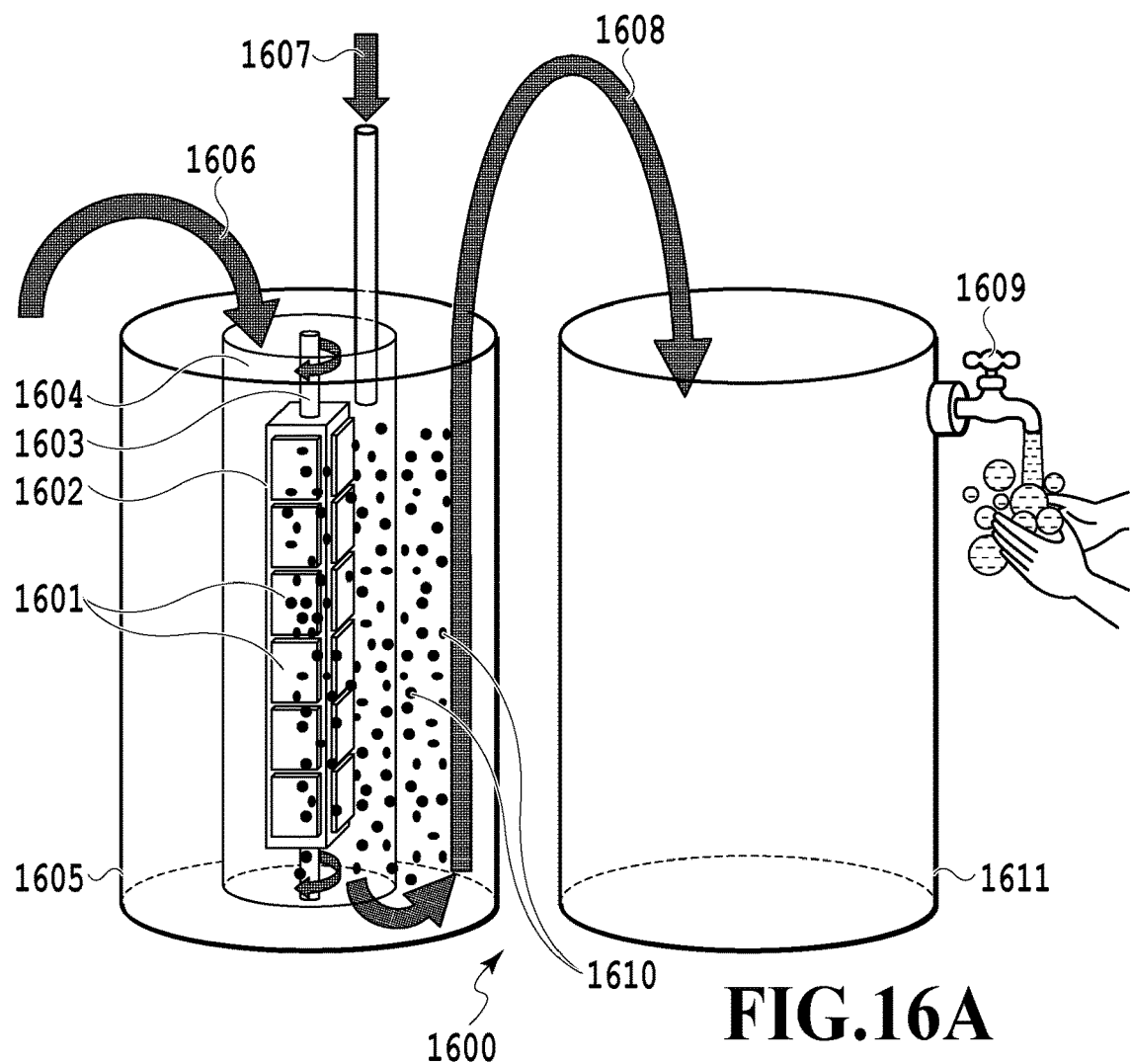
FIG. 16A is a diagram illustrating a UFB-containing liquid manufacturing apparatus in a tenth embodiment of the present invention.

FIG. 16A is a schematic configuration diagram of a bubble generating apparatus in a tenth embodiment of the present invention, which is incorporated into a water purifier 1600 serving as a bubble-containing liquid manufacturing apparatus. In addition to the configuration of the ninth embodiment, the present embodiment comprises a water storage tank 1611.

UFBs 1610 generated in the same manner as the ninth embodiment are stored in the water storage tank 1611 through a pipe 1608 and are discharged from a tap 1609 by turning the tap 1609 on. Ozone gas is blown from a gas blowing port 1607 into tap water inside a first water storage container 1604. Since large bubbles of the ozone gas float up against a flow of tap water inside the first water storage container 1604 due to buoyancy exerted on them, they are prevented from flowing in between the first water storage container 1604 and a second water storage container 1605. The volume of the water storage tank 1611 can be set according to its purpose and the like. In the present embodiment, the water storage tank 1611 has a volume of 100 L.

10,000 heaters were provided on one substrate 1601, and 10 substrates 1601 were mounted on each of the four side surfaces of a holding member 1602, with the result that 40 substrates 1601 were mounted in total. To the heaters, a pulse signal (pulse width: 0.7 μs, voltage: 26 V) was applied at a driving frequency of 20 kHz. A flow velocity of tap water supplied from a supply port 1606 was set at 1.0 L/min. It should be noted that the water storage tank 1611 is equipped with an unshown high-water sensor so that the supply of tap water from the supply port 1606 is automatically stopped in a case where the amount of water stored in the water storage tank 1611 exceeds 90.0 L. Ozone gas was continuously blown from the gas blowing port 1607 into the tap water inside the first water storage container 1604.

$$\text{Total Number of Heaters} = 1.0e4 \times 40 = 4.0e5 (= 4.0 \times 10^5)$$

Number of *UFBs* Generated =

$$(4.0e5) \times 1.0 \times (2.0e4) \times 60[s] = 2.88e13((UFBs/L)/h)$$

Figure 16B:
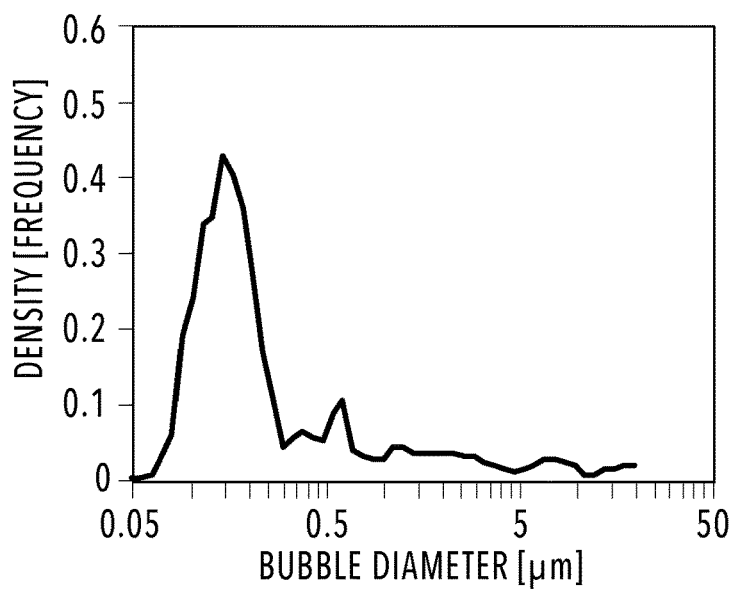
FIG. 16B is a graph illustrating the UFB-containing liquid manufacturing apparatus in the tenth embodiment of the present invention.

About 28.8 billion UFBs 1610 per ml were generated in one hour. The UFBs 1610 were thus generated in a high number density within an extremely short time. To confirm that, the collected tap water was set in the measurement device SALD-7500 (available from Shimadzu Corp.). As a result of measurement, a number density of UFBs 1610 with a diameter of less than 1.0 μm in the tap water was about 28.8 billion per ml. A frequency distribution of bubble diameter at that time is shown in FIG. 16B. The number of UFBs 1610 with a diameter ranging from 10 nm to 400 nm was 99.8% of the whole. Further, the number of UFBs 1610 generated in one series of steps from the stages (a) through (f) in FIG. 3 was about 1.0. Gas contained in the UFBs 1610 generated in the above manner was analyzed by the GC-TCD method as in the second embodiment. As a result of the analysis, ozone was detected. The amount of ozone detected was 10 [mg/L].

Eleventh Embodiment

Figure 17A:
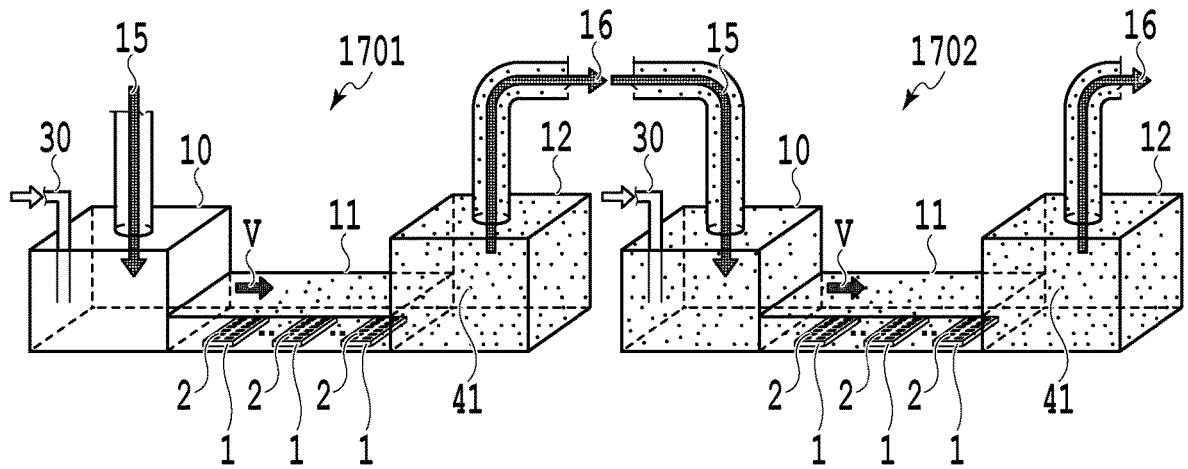
FIG. 17A is a diagram illustrating a UFB-containing liquid manufacturing apparatus in an eleventh embodiment of the present invention.
Figure 17B:
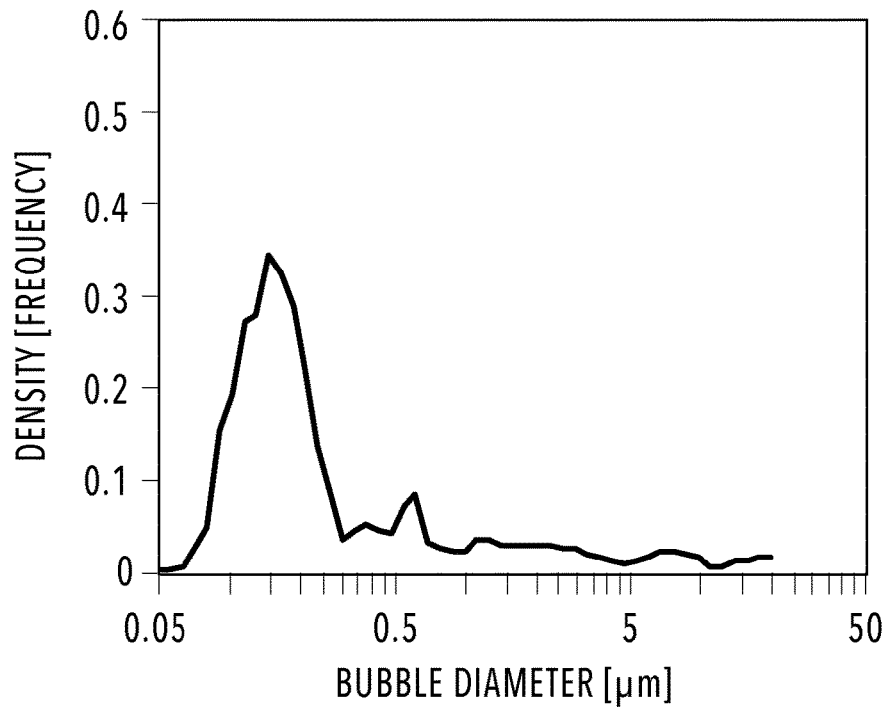
FIG. 17B is a graph illustrating the UFB-containing liquid manufacturing apparatus in the eleventh embodiment of the present invention.

FIG. 17A and FIG. 17B are diagrams illustrating an eleventh embodiment of the present invention. In the present embodiment, manufacturing apparatuses (first and second manufacturing apparatuses 1701 and 1702), each having the same function as that of the bubble-containing liquid manufacturing apparatus of the second embodiment shown in FIG. 5A, are connected in series. This enabled generation of UFBs twice the UFBs generated in the second embodiment, that is, about 2.4 billion UFBs 41 per ml in one minute. The UFBs 41 were thus generated in a high number density within an extremely short time. To confirm that, the collected tap water was set in the measurement device SALD-7500 (available from Shimadzu Corp.). As a result of measurement, a number density of UFBs 41 with a diameter of less than 1.0 μm in the tap water was about 2.4 billion per ml. A frequency distribution of bubble diameter at that time is shown in FIG. 17B. The number of UFBs 41 with a diameter ranging from 10 nm to 400 nm was 99.8% of the whole. Gas contained in the UFBs generated in the above manner was analyzed by the GC-TCD method as in the first embodiment. As a result of the analysis, nitrogen was detected. The components of the tap water were also analyzed. As a result of the analysis, no increase in impurities was detected.

The configuration of FIG. 22 shown as the modification of the first embodiment is also applicable to the present embodiment. For example, providing the manufacturing apparatus 1702 in FIG. 17 with the circulation mechanism shown in FIG. 22 enables more efficient generation of UFB-containing liquid of a high number density.

Twelfth Embodiment

Figure 18A:
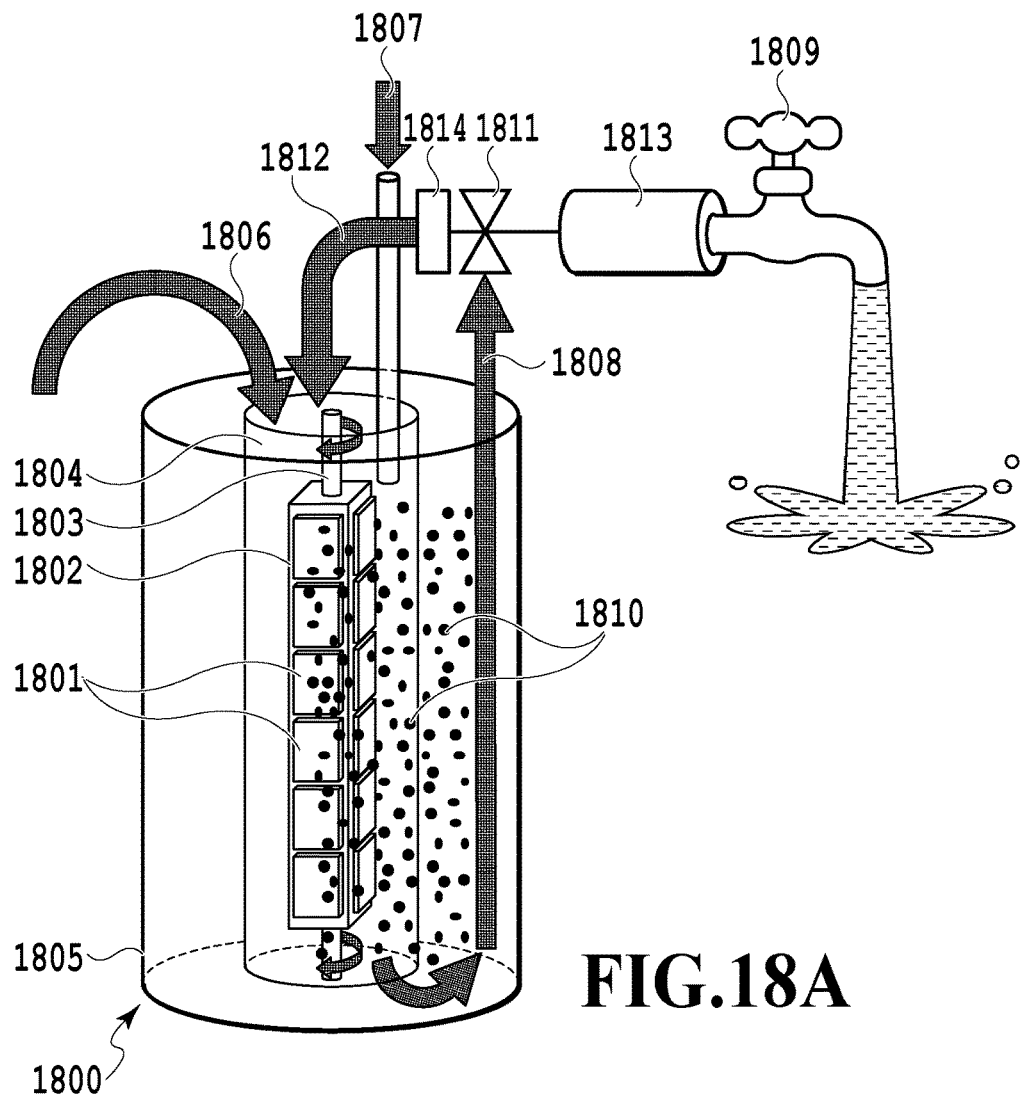
FIG. 18A is a diagram illustrating a UFB-containing liquid manufacturing apparatus in a twelfth embodiment of the present invention.

FIG. 18A is a schematic configuration diagram of a bubble generating apparatus in a twelfth embodiment of the present invention, which is incorporated into a water purifier 1800 serving as a bubble-containing liquid manufacturing apparatus. In addition to the configuration of the ninth embodiment shown in FIG. 15A, the present embodiment comprises a valve 1811 and a water flow source 1814 to form a circulation channel.

In the present embodiment, tap water containing UFBs 1810 in a higher number density is manufactured by forming a circulation channel through which tap water between a first water storage container 1804 and a second water storage container 1805 is returned to the inside of the first water storage container 1804 through a pipe 1808 and the valve 1811. This circulation channel comprises the water flow source 1814 which generates a water flow to circulate tap water in directions shown by arrows in FIG. 18A. As the water flow source 1814, various pumps can be used.

Tap water inside the first water storage container 1804 containing UFBs 1810 flows downward along a flow of tap water inside the first water storage container 1804 while being stirred by the rotation of a holding member 1802. Then, the tap water flows in between the first water storage container 1804 and the second water storage container 1805 from the lower end of the first water storage container 1804 and is discharged from a tap 1809 through a pipe 1808 by turning the tap 1809 on. Nitrogen gas is blown from a gas blowing port 1807 into the tap water inside the first water storage container 1804.

Since large bubbles of the nitrogen gas float up against the flow of tap water inside the first water storage container 1804 due to buoyancy exerted on them, they are prevented from flowing in between the first water storage container 1804 and the second water storage container 1805.

As in the ninth embodiment, 10,000 heaters were provided on one substrate 1801, and 25 substrates 1801 were mounted on each of the four side surfaces of a holding member 1802, with the result that 100 substrates 1801 were mounted in total. To the heaters, a pulse signal (pulse width: 5.0 µs, voltage: 18 V) was applied at a driving frequency of 20 kHz. A flow velocity of tap water supplied from a supply port 1806 was set at 1.0 L/min. It should be noted that the second water storage container 1805 is equipped with an unshown high-water sensor so that the supply of tap water from the supply port 1806 is automatically stopped in a case where the amount of water stored in the second water storage container 1805 exceeds 10.0 L. Nitrogen gas was continuously blown from the gas blowing port 1807 into the tap water inside the first water storage container 1804.

$$\text{Total Number of Heaters} = 1.0e4 \times 100 = 1.0e6 (= 1.0 \times 10^6)$$

Number of *UFBs* Generated =

$$(1.0e6) \times 1.0 \times (2.0e4) \times 60[s] = 1.2e12 ((UFBs/L)/\min)$$

About 1.2 billion UFBs 1810 per ml were generated in one minute. The UFBs 1810 were thus generated in a high number density within an extremely short time. Further, while stopping the supply of tap water from a supply port 1806 into the first water storage container 1804, tap water between the first water storage container 1804 and the second water storage container 1805 was returned to the inside of the first water storage container 1804 via the valve 1811 for circulation. This circulation was repeated ten times.

Number of *UFBs* Generated =

$$(1.0e7) \times 1.0 \times (2.0e4) \times 60[s] = 1.2e13 ((UFBs/L)/\min)$$

Figure 18B:
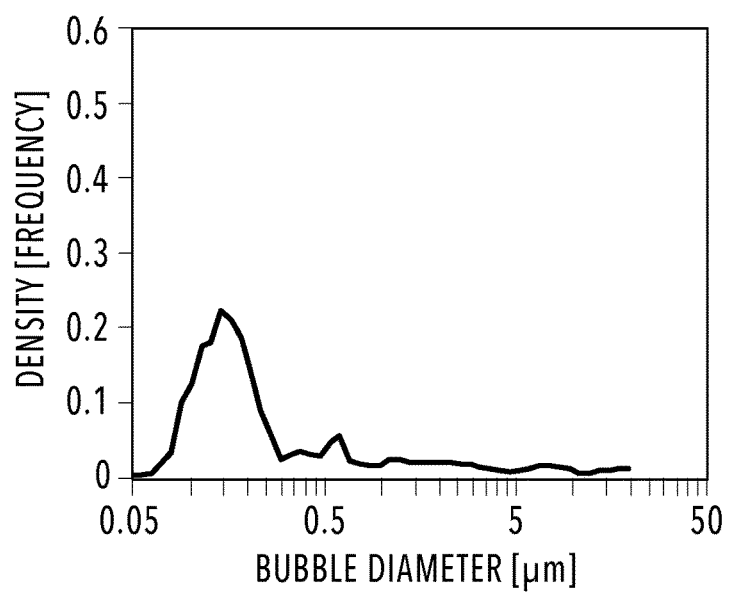
FIG. 18B is a graph illustrating the UFB-containing liquid manufacturing apparatus in the twelfth embodiment of the present invention.

About 12.0 billion UFBs 1810 per ml were generated in one minute. To confirm that, the collected tap water was set in the measurement device SALD-7500 (available from Shimadzu Corp.). As a result of measurement, a number density of UFBs 1810 with a diameter of less than 1.0 µm in the tap water was about 12.0 billion per ml. A frequency distribution of bubble diameter at that time is shown in FIG. 18B. The number of UFBs 1810 with a diameter ranging from 10 nm to 400 nm was 99.9% of the whole. Gas contained in the UFBs 1810 generated in the above manner was analyzed by the GC-TCD method as in the second embodiment. As a result of the analysis, nitrogen was detected. The components of the tap water were also analyzed. As a result of the analysis, no increase in impurities was detected. Such tap water containing UFBs 1810 is discharged from the tap 1809 through a pipe 1813 by turning the tap 1809 on.

Thirteenth Embodiment

The UFB-containing liquid manufactured in each of the embodiments described above was checked as to its bactericidal effect. As a method for checking, a bactericidal test method for laundry detergent was carried out.
A Test Condition is Described Below.
Test Temperature: 25° C.
Test Period: 5 Minutes
Test Container: Stainless Plate
Test Bacterial Species: *Staphylococcus Aureus, Escherichia Coli*
Test Bacterial Solution Density: 1.25e8 to 6.25e8 [cfu/ml]
Test Sample: 0.1 mL As test targets A to E, UFB-containing liquids (UFB waters) manufactured in the seventh, ninth, tenth, eleventh, and twelfth embodiments were each prepared in an amount of 10 ml. As described above, ozone was injected into the UFB-containing liquids in the seventh and tenth embodiments and nitrogen was injected into the UFB-containing liquids in the ninth, eleventh, and twelfth embodiments. Further, as comparison targets A to E, raw waters before UFB generation used in the seventh, ninth, tenth, eleventh, and twelfth embodiments were each prepared in an amount of 10 ml.

Test Target A: 10 ml of UFB Water Manufactured in Seventh Embodiment (Ozone; 2.4 billion UFBs per ml)
Test Target B: 10 ml of UFB Water Manufactured in Ninth Embodiment (Nitrogen; 1.2 billion UFBs per ml)
Test Target C: 10 ml of UFB Water Manufactured in Tenth Embodiment (Ozone; 28.8 billion UFBs per ml)
Test Target D: 10 ml of UFB Water Manufactured in Eleventh Embodiment (Nitrogen; 2.4 billion UFBs per ml)
Test Target E: 10 ml of UFB Water Manufactured in Twelfth Embodiment (Nitrogen; 12.0 billion UFBs per ml)
Comparison Target A: 10 ml of Pure Water Used in Seventh Embodiment
Comparison Target B: 10 ml of Tap Water Used in Ninth Embodiment
Comparison target C: 10 ml of Tap Water Used in Tenth Embodiment
Comparison Target D: 10 ml of Tap Water Used in Eleventh Embodiment
Comparison Target E: 10 ml of Tap Water Used in Twelfth Embodiment A test solution containing *Staphylococcus aureus* and a test solution containing *Escherichia coli* were immersed in the above ten types of liquids. Then, the solutions after the immersion test were treated and the number of viable bacteria was measured. Changes in the number of viable bacteria before and after the treatment are shown in FIG. 19.

As is obvious from FIG. 19, *Staphylococcus aureus* and *Escherichia coli* were almost made harmless by the immersion for five minutes in the UFB waters of the test targets A to E. In contrast, *Staphylococcus aureus* and *Escherichia coli* remained unchanged in the waters of the comparative targets A to E. This showed that the UFB waters prepared in the present invention have the effect of killing *Staphylococcus aureus* and *Escherichia coli* almost entirely.

Fourteenth Embodiment

Figure 20A:
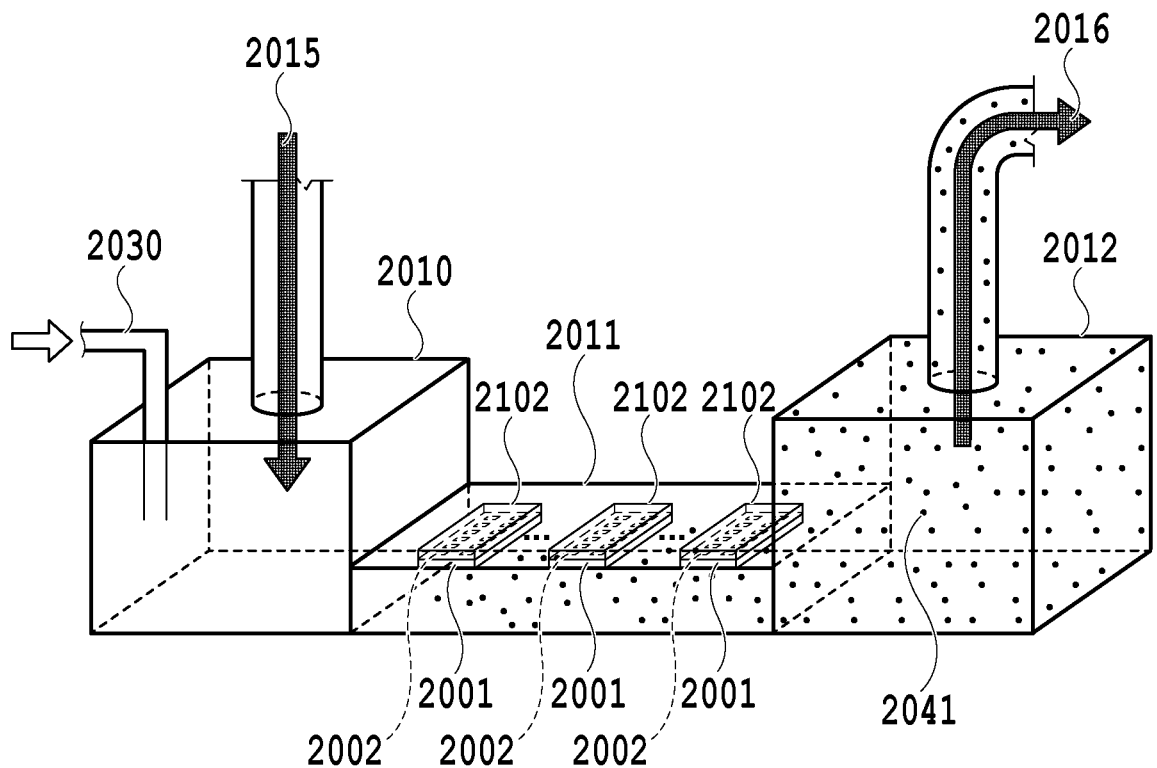
FIG. 20A is a diagram illustrating a UFB-containing liquid manufacturing apparatus in a fourteenth embodiment of the present invention.

FIG. 20A is a schematic configuration diagram of a bubble generating apparatus in a fourteenth embodiment of the present invention. The generating apparatus is incorporated into a bubble-containing liquid manufacturing apparatus. The present embodiment is different from the embodiments described above in the configuration of substrates 2001, the arrangement of the substrates 2001 and the like.

A water flow channel 2011 is formed between a water supply tank 2010 and a water storage tank 2012. Tap water is supplied from a water supply channel 2015 to the water supply tank 2010. The tap water flows through the water flow channel 2011 at a flow velocity V, is stored in the water storage tank 2012, and is then discharged through a discharge channel 2016. In the water flow channel 201, a substrate 2001 having heating resistance elements (heaters) 2002 as a source of UFBs are provided like the substrate 1 having the heating resistance elements (heaters) 2 shown in FIG. 1. In the present embodiment, 10,000 heaters 2002 were provided on one substrate 2001 as in the first embodiment, and 20 substrates 2001 in total were mounted side by side. To the heaters 2002, a pulse signal (pulse width: 1.0 μs, voltage: 24V) was applied at a driving frequency of 20 kHz. Tap water was supplied to the water flow channel 2011 and its flow velocity V was set at 1.0 L/min. At that time, nitrogen gas was injected from a gas injection port 2030 into the tap water inside the water supply tank 2010 to make the tap water bubble, thereby converting most of the gas dissolved in the tap water inside the water supply tank 2010 into nitrogen gas.

Figure 21A:
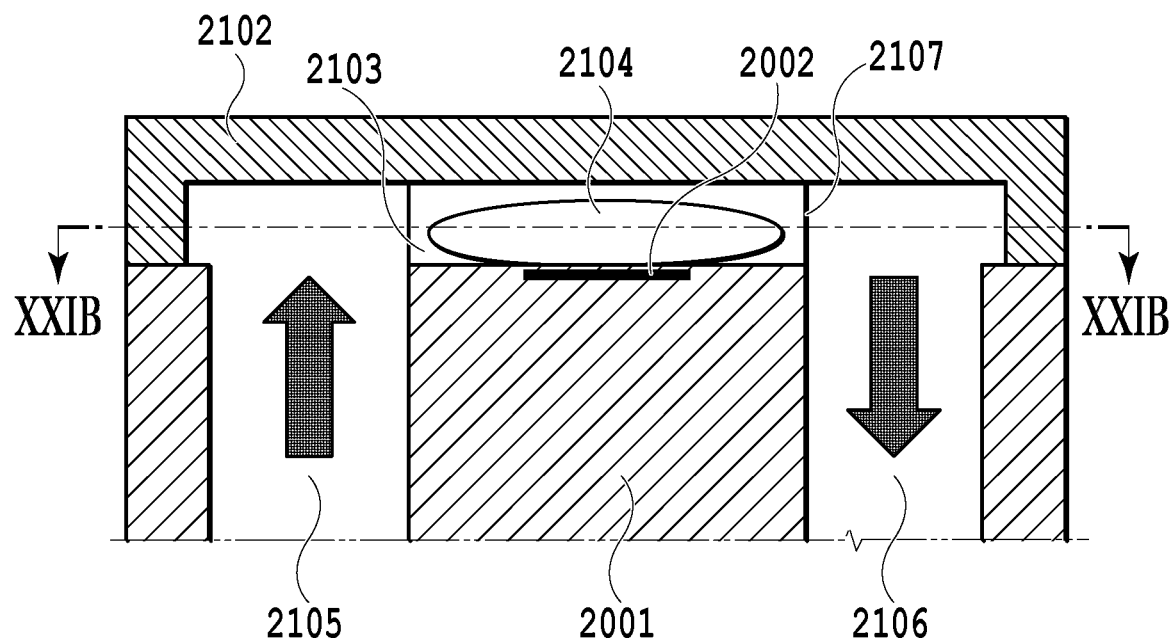
FIG. 21A is a cross-sectional view of a substrate in FIG. 20A.
Figure 21B:
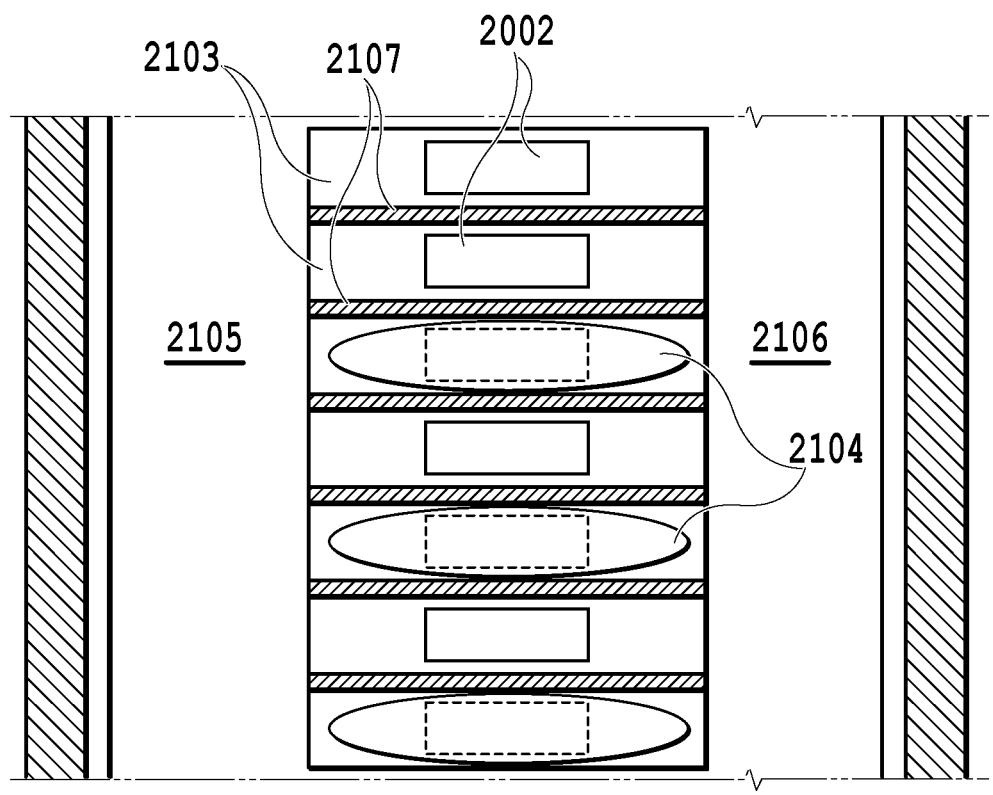
FIG. 21B is a cross-sectional view of the substrate in FIG. 20A.

FIG. 21A is an enlarged cross-sectional view of the substrate 2001 including the heaters 2002. FIG. 21B is a cross-sectional view seen along XXIB-XXIB in FIG. 21A. The heaters 2002 are provided on the substrate 2001. A channel member 2102 is provided above the heaters 2002 to form liquid flow channels 2103. Tap water containing unshown dissolved gas (nitrogen gas) is supplied from a liquid supply port 2105 to the liquid flow channels 2103 along the flow inside the water flow channel 2011 shown in FIG. 20A and is then discharged from a liquid discharge port 2106.

As shown in FIG. 21B, the liquid flow channels 2013 are defined by channel wall members 2107 to correspond to the heaters 2002, respectively. That is, one liquid flow channel 2013 is formed for each heater 2002. As shown in FIG. 20A, the substrates 2001 are provided in the upper part of the water flow channel 2011 to direct the heaters 2002 above. In FIG. 20A, the inner upper surface of the water flow channel 2011 faces the upper surface of the channel member 2102. The water flow channel 2011 may form at last part of the channel member 2102. Since the substrates 2001 are provided in the upper part inside the water flow channel 2011, UFBs 2041 generated in the manner as the stages (a) through (f) in FIG. 3 are discharged downward from the liquid discharge port 2106 together with tap water.

In the case of generating UFBs 2041, a bubble 2104 is generated by film boiling of tap water like the bubble 320 shown in FIG. 3. Since the bubble 2104 grows inside each of the liquid flow channels 2013 regulated to correspond to the respective heaters 2002, bubbles 2104 in adjacent liquid flow channels 2013 do not interfere with each other. Accordingly, a plurality of heaters 2002 can be arranged in high density and UFBs 2041 can be efficiently generated by means of the heaters 2002. The growth direction of the bubble 2104 is regulated by the four surfaces defining the liquid flow channel 2013: the upper surface of the substrate 2001, the lower surface of the channel member 2102, and the inner surfaces of the left and right (upper and lower in FIG. 21B) channel wall members 2107. However, the position of the bubble 2104 may be regulated by at least one of the left and right channel wall members 2107, or only by the channel member 2102. Alternatively, the position of the bubble 2104 may be regulated by the channel member 2102 and either of the left and right channel wall members 2107. In short, it is only necessary to regulate at least part of the position of the bubble 2104.

$$\text{Total Number of Heaters} = 1.0e4 \times 20 = 2.0e5 (= 2.0 \times 10^5)$$

Number of UFBs Generated =

$$(2.0e5) \times 10 \times (2.0e4) \times 60[s] = 2.4e12 ((UFBs/L)/\min)$$

Figure 20B:
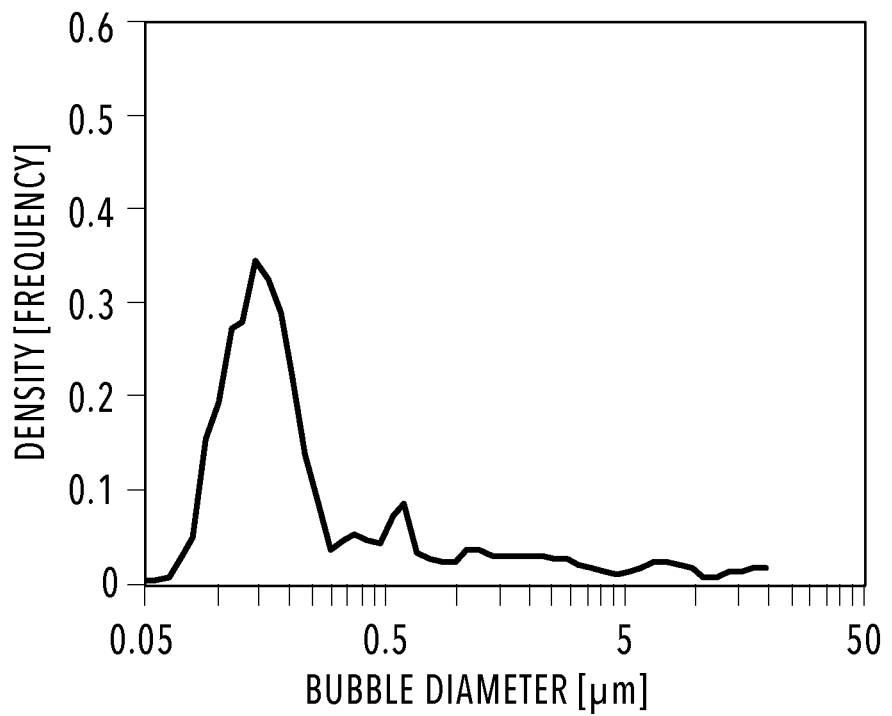
FIG. 20B is a graph illustrating the UFB-containing liquid manufacturing apparatus in the fourteenth embodiment of the present invention.

About 2.4 billion UFBs 2041 per ml were generated in one minute. The UFBs 2041 were thus generated in a high number density within an extremely short time. To confirm that, the collected tap water was set in the measurement device SALD-7500 (available from Shimadzu Corp.). As a result of measurement, a number density of UFBs 2041 with a diameter of less than 1.0 μm in the tap water was about 2.4 billion per ml. A frequency distribution of bubble diameter at that time is shown in FIG. 20B. The number of UFBs 2041 with a diameter ranging from 10 nm to 400 nm was 99.0% of the whole. Gas contained in the UFBs generated in the above manner was analyzed by the GC-TCD method as in the first embodiment. As a result of the analysis, nitrogen was detected. The components of the tap water were also analyzed. As a result of the analysis, no increase in impurities was detected.

The configuration of FIG. 22 shown as the modification of the first embodiment is also applicable to the present embodiment. For example, providing the manufacturing apparatus in FIG. 20 with the circulation mechanism shown in FIG. 22 enables more efficient generation of UFB-containing liquid of a high number density.

OTHER EMBODIMENTS

In the present invention, UFBs with a diameter of less than 1.0 μm can be efficiently generated in a short time by causing film boiling exceeding transition boiling in liquid. As an example of a source of UFBs, heating resistance units each having the shape of a square or rectangle of several tens of micrometers may be used. Even if 10,000 heating resistance units are formed, the total size can be within several millimeters. As a result, the size of the UFB-containing liquid manufacturing apparatus can be greatly reduced. Further, forming each UFB source into the shape of a square or rectangle of several tens of micrometers can improve the efficiency of UFB generation and downsize the liquid supply tank and the liquid discharge tank (container).

Examples of a condition for causing film boiling are described below. Film boiling occurred in liquid in a case where the liquid was heated by a heater for a period of 100 μsec or less. Further, film boiling occurred in liquid in a case where a width of a surface of a heating portion including a heater in contact with the liquid was 5.00 mm or less, the other width was 5.00 mm or less, and the area of the surface in contact with the liquid was 25.0 mm² or less. The occurrence of film boiling in liquid increased the number of ultrafine bubbles contained in the liquid to 2.0 billion or more per ml. In addition, 50% or more of the ultrafine bubbles contained in the liquid had a diameter ranging from 10 nm to 400 nm. The ultrafine bubbles thus generated was reduced by 50% or less after a week. Further, since ultrafine bubbles including gas therein were contained in an ultrafine bubble-containing liquid, the gas was contained in an amount equal to or greater than the saturation solubility of the gas dissolved in liquid under atmospheric pressure.

The liquid is not limited to one containing water as a main ingredient in the above embodiments and may include, for example, an organic solvent, chlorine compound, and electrolyte ion. The chlorine compound is, for example, LiCL, KCL, NACL, $MgCL_2$, or $CaCL_2$, and is dissolved in liquid in an amount equal to or less than its solubility. The electrolyte ion is, for example, sodium (Na), potassium (K), calcium (Ca), magnesium (Mg), manganese (Mn), phosphorus (P), chlorine (Cl), or bicarbonate ($HCO_3^-$), and is dissolved in liquid in an amount equal to or less than its solubility. Further, a gas inside ultrafine bubbles can be selected as appropriate by dissolving a desired type of gas in liquid. As the gas, for example, it is possible to include a gas selected from the group consisting of hydrogen, helium, oxygen, nitrogen, methane, fluorine, neon, carbon dioxide, ozone, argon, chlorine, ethane, propane, air, and gaseous mixtures thereof.

In order to improve the effect of the present invention, it is preferable to remove a gas component dissolved in water to be supplied. That is, water is prepared by removing a desired amount of dissolved gas by degassing means, and then a gas to be dissolved is injected into the degassed water. UFBs including the desired gas can be generated by heating the liquid in which the desired gas is dissolved by means of a heater and causing film boiling.

The present invention is applicable to not only the above embodiments but also combinations of the configurations and conditions of the above embodiments. For example, the present invention is applicable as an ultrafine bubble-containing liquid manufacturing apparatus and ultrafine bubble generating method used for various apparatuses that make use of ultrafine bubbles.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Applications No. 2017-167594, filed Aug. 31, 2017, and No. 2018-148537, filed Aug. 7, 2018, which are hereby incorporated by reference wherein in their entirety.

REFERENCE SIGNS LIST 1 element substrate
2 heater
41 ultrafine bubble (UFB)
11 water flow channel
212 liquid ejection element
320 bubble
700 liquid ejection unit

The invention claimed is:

1. An ultrafine bubble-containing liquid manufacturing apparatus, comprising:
   a storage unit configured to store liquid in a position including a predetermined region; and
   a heating unit configured to generate ultrafine bubbles smaller than 1.0 µm in diameter in the liquid by heating the liquid in the predetermined region and causing film boiling; and
   a collector configured to collect the liquid containing the ultrafine bubbles.

2. The ultrafine bubble-containing liquid manufacturing apparatus according to claim 1, wherein the heating unit includes a heating resistance portion.

3. The ultrafine bubble-containing liquid manufacturing apparatus according to claim 1, further comprising a control unit configured to heat the heating unit intermittently to cause the film boiling intermittently.

4. The ultrafine bubble-containing liquid manufacturing apparatus according to claim 1, further comprising a channel in which the liquid flows through the predetermined region.

5. The ultrafine bubble-containing liquid manufacturing apparatus according to claim 1, further comprising a circulation channel configured to circulate the liquid through the predetermined region.

6. The ultrafine bubble-containing liquid manufacturing apparatus according to claim 1, further comprising:
   a pressure chamber including at least part of the predetermined region;
   a supply channel for supplying the liquid to the pressure chamber; and
   an ejection opening communicating with the pressure chamber,
   wherein the liquid inside the pressure chamber is ejected from the ejection opening by energy of bubbles generated by the film boiling in the liquid.

7. The ultrafine bubble-containing liquid manufacturing apparatus according to claim 6, wherein the collector is configured to collect the liquid ejected from the ejection opening.

8. The ultrafine bubble-containing liquid manufacturing apparatus according to claim 1, further comprising an injection unit configured to inject gas into the liquid.

* * * * *